(12) United States Patent
Yamashita et al.

(10) Patent No.: US 11,730,772 B2
(45) Date of Patent: Aug. 22, 2023

(54) LIPOPOLYSACCHARIDE-REGULATED ENTERIC BACTERIA AND USE THEREOF

(71) Applicant: NOSTER INC., Muko (JP)

(72) Inventors: Tomoya Yamashita, Hyogo (JP); Takuo Emoto, Hyogo (JP); Naofumi Yoshida, Hyogo (JP)

(73) Assignee: NOSTER INC., Muko (JP)

( * ) Notice: Subject to any disclaimer, the term of this patent is extended or adjusted under 35 U.S.C. 154(b) by 181 days.

(21) Appl. No.: 16/968,376

(22) PCT Filed: Feb. 8, 2019

(86) PCT No.: PCT/JP2019/004763
§ 371 (c)(1),
(2) Date: Aug. 7, 2020

(87) PCT Pub. No.: WO2019/156251
PCT Pub. Date: Aug. 15, 2019

(65) Prior Publication Data
US 2020/0390828 A1    Dec. 17, 2020

(30) Foreign Application Priority Data
Feb. 9, 2018   (JP) ................ 2018-022578

(51) Int. Cl.
| | | |
|---|---|---|
| A01N 63/00 | (2020.01) | |
| A61K 35/74 | (2015.01) | |
| A23L 33/135 | (2016.01) | |
| C12N 1/20 | (2006.01) | |

(52) U.S. Cl.
CPC ............ *A61K 35/74* (2013.01); *A23L 33/135* (2016.08); *C12N 1/20* (2013.01)

(58) Field of Classification Search
CPC .................................................. A61K 35/74
See application file for complete search history.

(56) References Cited

FOREIGN PATENT DOCUMENTS

| CN | 104546942 A | 4/2015 | |
|---|---|---|---|
| JP | 4-330016 A | 11/1992 | |
| JP | 2013-527240 A | 6/2013 | |
| WO | 2011/153226 A2 | 12/2011 | |
| WO | 2012/142605 A1 | 10/2012 | |
| WO | 2014/145958 A2 | 9/2014 | |
| WO | 2016/086210 A1 | 2/2016 | |
| WO | 2017/160711 A1 | 9/2017 | |
| WO | WO-2018152306 A1 * | 8/2018 | ............ A61K 35/74 |

OTHER PUBLICATIONS

Extended European Search Report, dated Sep. 21, 2021, issued by the European Patent Office in corresponding European Patent Application No. 19750410.3.
Hirata et al., The Journal of the Japanese Society of International Medicine, 2016, vol. 105, No. 9, pp. 1706-1711 (total 11 pages).
Emoto et al., "Analysis of Gut Microbiota in Coronary Artery Disease Patients: a Possible Link between Gut Microbiota and Coronary Artery disease", J. Atheroscler. Thromb., 2016, vol. 23, pp. 908-921.
Davis-Richardson et al., "*Bacteroides dorei* dominates gut microbiome prior to autoimmunity in Finnish children at high risk for type 1 diabetes", Frontiers in Microbiology, 2014, vol. 5, doi:10.3389/fmicb.2014.00678, pp. 1-11 (total 11 pages).
Pedersen et al., "Species differentiation of *Bacteroides dorei* from *Bacteroides vulgatus* and *Bacteroides ovatus* from *Bacteroides xylanisolvens*—Back to basics", Anaerobe, vol. 24, 2013, pp. 1-3 (total 3 pages).
Yoshida et al., "*Bacteroides vulgatus* and *Bacteroides dorei* Reduce Gut Microbial Lipopolysaccharide Production and Inhibit Atherosclerosis", Circulation, Nov. 2018, vol. 138. pp. 2486-2498 (total 13 pages).
Karlsson et al., "Symptomatic atherosclerosis is associated with an altered gut metagenome", Nature Communications, Dec. 4, 2012, 3:1245, pp. 1-8 (total 8 pages).
Yin et al., "Dysbiosis of Gut Microbiota With Reduced Trimethylamine-N-Oxide Level in Patients With Large-Artery Atherosclerotic Stroke or Transient Ischemic Attack", J. Am. Heart Assoc. 4, E002699 (2015), pp. 1-12 (total 12 pages).
Emoto et al., "Characterization of gut microbiota profiles in coronary artery disease patients using data mining analysis of terminal restriction fragment length polymorphism: gut microbiota could be a diagnostic marker of coronary artery disease", Heart Vessels. 32, (2017), pp. 39-46 (total 8 pages).
Jie et al., "The gut microbiome in atherosclerotic cardiovascular disease", Nature Communications, 8, 845 (2017), pp. 1-12 (total 12 pages).
Patel et al., "Human Experimental Endotoxemia in Modeling the Pathophysiology, Genomics and Therapeutics of Innate Immunity in Complex Cardiometabolic Diseases", Arterioscler. Thromb. Vasc. Biol., Mar. 2015, 35(3), 525-534, pp. 1-21 (total 21 pages).
Kasahara et al., "Commensal bacteria at the crossroad between cholesterol homeostasis and chronic inflammation in atherosclerosis", Journal of Lipid Research, vol. 58, 2017, pp. 519-528 (total 10 pages).
Vatanen et al., "Variation in Microbiome LPS Immunogenicity Contributes to Autoimmunity in Humans", Cell, May 5, 2016, 165(4), pp. 842-853 (total 25 pages).
International Search Report, dated May 14, 2019, in International Application No. PCT/JP2019/004763.

* cited by examiner

*Primary Examiner* — Albert M Navarro
(74) *Attorney, Agent, or Firm* — Sughrue Mion, PLLC

(57) ABSTRACT

The present invention provides a combination containing (1) a composition containing a live bacterium of *Bacteroides vulgatus* isolated from nature, and (2) a composition containing a live bacterium of *Bacteroides dorei* isolated from nature.

9 Claims, 17 Drawing Sheets
Specification includes a Sequence Listing.

| | | |
|---|---|---|
| Query | 12 | AGAGTTTGATCCTGGCTCAGGATGAACGCTAGCTACAGGCTTAACACATGCAAGTCGAGG 71 |
| Sbjct | 1 | AGAGTTTGATCCTGGCTCAGGATGAACGCTAGCTACAGGCTTAACACATGCAAGTCGAGG 60 |
| Query | 72 | GGCAGCATGGTCTTAGCTTGCTAAGGCCGATGGCGCACCGGGTGAGTAACACGT 131 |
| Sbjct | 61 | GGCAGCATGGTCTTAGCTTGCTAAGGCCGATGGCGCACCGGGTGAGTAACACGT 120 |
| Query | 132 | ATCCAACCTGCGTCTACTCTGGACAGCAGCCTTCTGAAAGGAAGATTAATACAAGATGGCA 191 |
| Sbjct | 121 | ATCCAACCTGCGTCTACTCTGGCCAGCCTTCTGAAAGGAAGATTAATCCAGGATGGGA 180 |
| Query | 192 | TCATGAGTCCGCATGTTCACATGATTAAAGGTA-TTCCGGTAGACGATGGGGATGCGTT 249 |
| Sbjct | 181 | TCATGAGTTCACATGTCCGCATGATTAAAGGTATTTCCGGTAGACGATGGGGATGCGTT 240 |
| Query | 250 | CCATTAGATAGTAGCGGGGTAACGGCCCACCTAGTCTTCGATGGATAGGGGTTCTGAGA 309 |
| Sbjct | 241 | CCATTAGATAGTAGCGGGGTAACGGCCCACCTAGTCAACGATGGATAGGGGTTCTGAGA 300 |
| Query | 310 | GGAAGGTCCCCACATTGGAACTGAGACACGGTCCAAACTCTACGGAGGCAGCAGTGA 369 |
| Sbjct | 301 | GGAAGGTCCCCACATTGGGACTGAGACACGGTCCAAACTCCTACGGAGGCAGCAGTGA 360 |
| Query | 370 | GGAATATTGGTCAATGGGCGAGAGCCTGAACCAGCCAAGCCGTGAAGGATGACTGCC 429 |
| Sbjct | 361 | GGAATATTGGTCAATGGGCGAGAGCCTGAACCAGCCAAGCCGTGAAGGATGATGACTGCCC 420 |
| Query | 430 | TATGGGTTGTAAACTTCTTTATAAAGGAATAAAGTCGGGTATGGATACCCGTTGCATG 489 |
| Sbjct | 421 | TATGGGTTGTAAACTTCTTTATAAAGGAATAAAGTCGGGTATGCATACCCGTTGCATG 480 |
| Query | 490 | TACTTTATGAATAAGGATCGGCTAACTCCGTGCCAGCAGCCGCGGTAATACGGAGGATCC 549 |
| Sbjct | 481 | TACTTTATGAATAAGGATCGGCTAACTCCGTGCCAGCAGCCGCGGTAATACGGAGGATCC 540 |
| Query | 550 | GAGCGTTATCCGGATTTATTGGGTTTAAAGGGAGCGTAGATGTTAAGTCAGTGT 609 |
| Sbjct | 541 | GAGCGTTATCCGGATTTATTGGGTTTAAAGGGAGCGTAGATGTTAAGTCAGTGT 600 |
| Query | 610 | GAAAGTTTGCGGCTCAACCGTAAAATTGCAGTTGATATCTTGAGTGCAGTGA 669 |
| Sbjct | 601 | GAAAGTTTGCGGCTCAACCGTAAAATTGCAGTTGATATCTTGAGTGCAGTGA 660 |
| Query | 670 | GGCAGGCGGAATTCGTGGTGTAGCGGTGAAATGCTTAGATATCACGAAGAACTCCGATTG 729 |
| Sbjct | 661 | GGCAGGCGGAATTCGTGGTGTAGCGGTGAAATGCTTAGATATCACGAAGAACTCCGATTG 720 |

```
Query   730   CGAAGGCAGCCTGCTAAGCTGCAACTGACATTGAGGCTCGAAAGTGTGGGTATCAAACAG   789
              ||||||||||||||||||||||||||||||||||||||||||||||||||||||||||||
Sbjct   721   CGAAGGCAGCCTGCTAAGCTGCAACTGACATTGAGGCTCGAAAGTGTGGGTATCAAACAG   780

Query   790   GATTAGATACCCTGGTAGTCCACACGGTAAACGATGAATACTCGCTGTTTGCGATATACT   849
              |||||||||||||||||||||||| ||||||||||||||||||||||||||||||||||
Sbjct   781   GATTAGATACCCTGGTAGTCCACACGGTAAACGATGAATACTCGCTGTTTGCGATATACG   840

Query   850   GCAAGCGGCCAAGCGAAAGCGTTAAGTATTCCACCTGTAAGTACGCCGGCAACGGTGAA   909
              |||||||||||||||||||||||||||||||||||||||||||||||||||||||||||
Sbjct   841   GCAAGCGGCCAAGCGAAAGCGTTAAGTATTCCACCTGGGAGTACGCCGGCAACGGTGAA   900

Query   910   GCAAGCGGCCAAGCGAAATGACGGGGGCCCGCACAAGCGGAGGAACATGGTTAATTCGATGAT   969
              ||||||||||||||||||||||||||||||||||||||||| || || ||||| |||||
Sbjct   901   ACTCAAAGGAATTGACGGGGGCCCGCACAAGCGGAGGAACAGCGGTTAATTCGATGAT   960

Query   970   ACTCAAAGGAATTGACGGGGGCCCGCACAAGCGGCTTAAATTGCAGATGAATTA-CGGTGAAAGCCGTA-AGC   1027
              ||||||||||||||||||||||||||||||| || | | || || ||||| |||| || ||| ||
Sbjct   961   ACGCGAGGAACCTTACCGGGCTTAAATTGCAGATGAATTA-CGGTGAAAGCCGTA-AGC   1018

Query   1028  ACGCGAGGAACCTTACCGGGCTTAAATTGCACTGATCC-GAAA-CGGTTCAGC   1078
              |||||||||||||||||||| ||||||||| ||||| | | | ||||| |||
Sbjct   1019  C-GCAAG-GCATCTGTGAAGGTGCATGGTTGTCGTCAGCTCGTGCCGTGAGGTGTCG   1085

Query   1079  TAGCAATAGCGAGTGTGAAGGTGCATGGTTGTCGTCAGCTCGTGCCGTGAGGTGTCG   1138
              |||||||||||||||||||||||||||||||| ||||||||||||||||||||||| 
Sbjct   1086  GCTTAAGTGCCATAACGAGCGCAACCCTTGTCTGTTGTTACTAACAGGTTACTGAGGA   1145

Query   1139  GCTTAAGTGCCATAACGAGCGCAACCCTGTCAGTTACTAACAGGTGATGCTGAGGA   1198
              |||||||||||||||||||||||||||||||||||||||||||||||||||||||
Sbjct   1146  CTCTGACAAGACTGCCAATCGCTAGTAATCGCGGATCAGCATGCCGCGGTGAATACG   1205

Query   1199  GCCCTTACGTCCGGGGATGCCAATCGCTAGTAATCGCGGATCAGCATGCCGCGGTGAATACG   1258
              |||||||||||||||||||||||||||||||||||||||||||||||||||||||||
Sbjct   1206  GCCCTTACGTCCGGGGATGCCAATCCCTAAAACCCTCTCAGTTCGGAGTCTGCAACCGACTC   1265

Query   1259  CGAGTGGATGCCAATCCCTAAAACCCTCTCAGTTCGGAGTCTGCAACCGACTC   1318
              ||||||||||||||||||||||||||||||||||||||||||||||||||||
Sbjct   1266  CACGAAGTCGAATCGCTAGTAATCGCGGATCCAAGCCATGGACGTGAATACGTTCCCGG   1325

Query   1319  CACGAAGTCGAATCGCTAGTAATCGCGGATCCAAGCCATGGACGTGAATACGTTCCCGG   1378
              ||||||||||||||||||||||||||||||||||||||||||||||||||||||||||
Sbjct   1326  CACTTGTACACACCGCCCGTCAAGCCATGGGAGTGGGCTAAGTGCGTAACCGC   1385

Query   1379  GCCTTGTACACACCGCCCGTCAAGCCATGGGAGTGGGCTAAGTGCGTAACCGC   1438
              ||||||||||||||||||||||||||||||||||||||||||||||||||||
Sbjct   1386  GAGGATCGCCCTAGGGTAAAACTGGTGACTGGGGCTAAGT-TAACAAGGTA   1490

Query   1439  GAGGATCGCCCTAGGGTAAAACTGGTGACTGGGGCTAAGT-TAACAAGGTA   1497
```

FIG. 11 (Continued)

Fig. 14-1
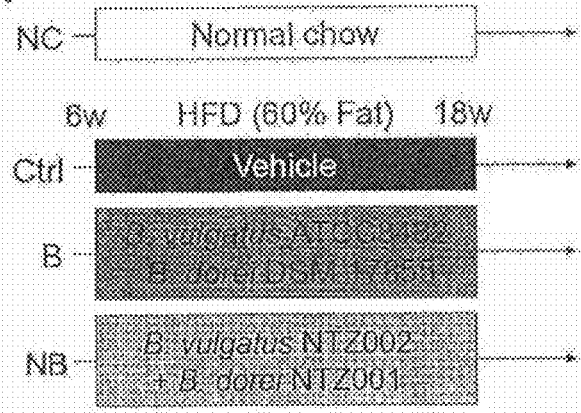
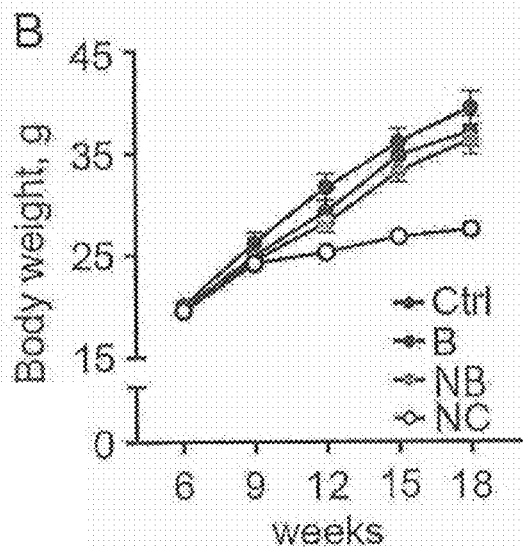
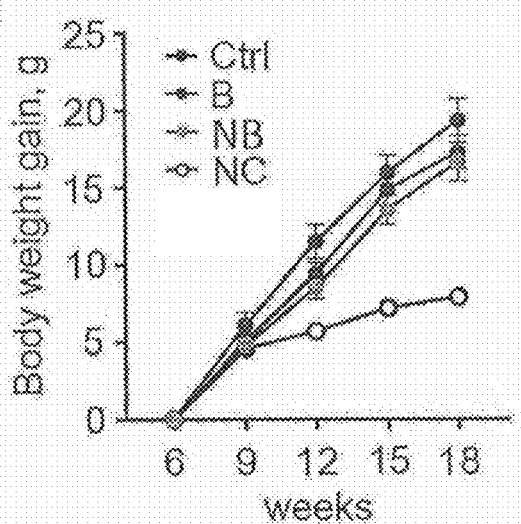
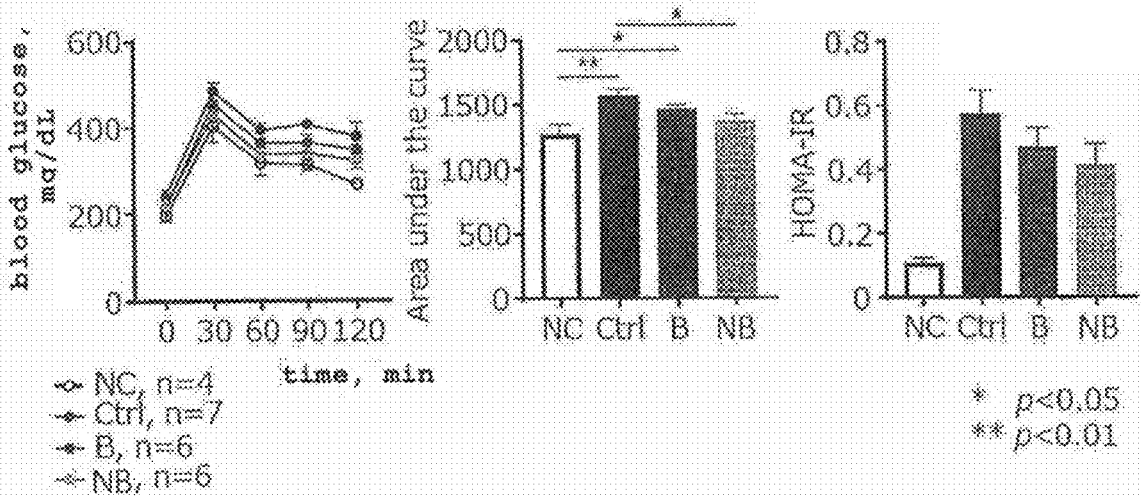
* $p<0.05$
** $p<0.01$

Fig. 15-1
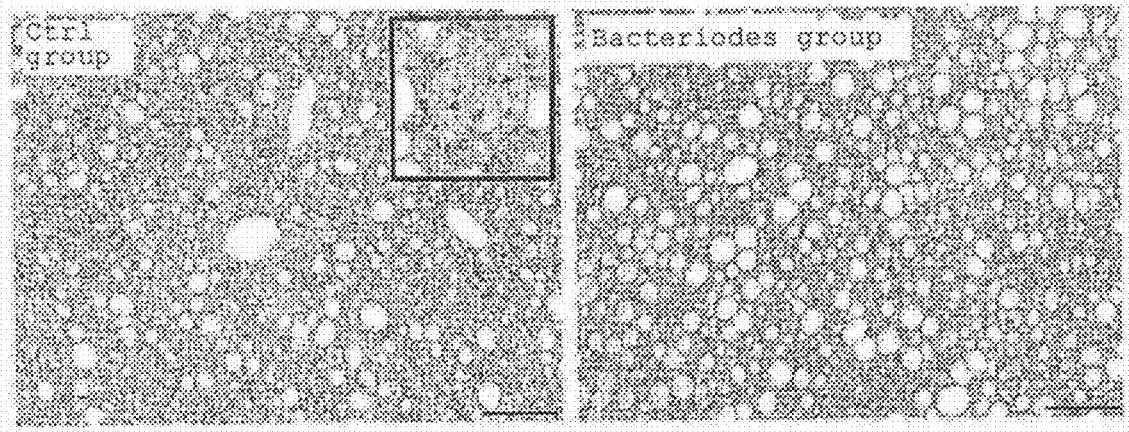
NAS
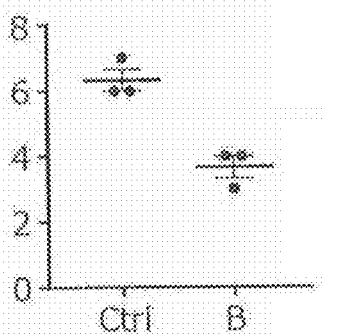
blood AST
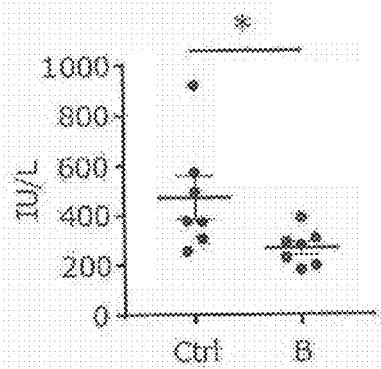
AST/ALT ratio
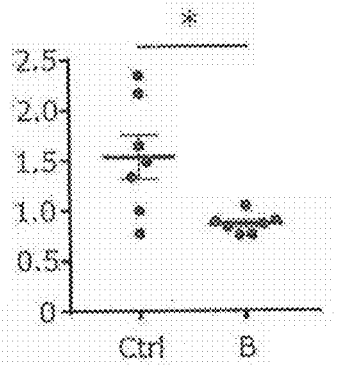
* $p<0.05$

SEQUENCE LISTING

```
<160> NUMBER OF SEQ ID NOS: 52

<210> SEQ ID NO 1
<211> LENGTH: 1510
<212> TYPE: DNA
<213> ORGANISM: Bacteroides vulgatus

<400> SEQUENCE: 1
tattacaatg aagagtttga tcctggctca ggatgaacgc tagctacagg cttaacacat      60
gcaagtcgag gggcagcatg gtcttagctt gctaaggccg atggcgaccg gcgcacgggt     120
gagtaacacg tatccaacct gccgtctact cttggacagc cttctgaaag gaagattaat     180
acaagatggc atcatgagtc cgcatgttca catgattaaa ggtattccgg tagacgatgg     240
ggatgcgttc cattagatag taggcggggt aacggcccac ctagtcttcg atggataggg     300
gttctgagag gaaggtcccc cacattggaa ctgagacacg gtccaaactc ctacgggagg     360
cagcagtgag gaatattggt caatgggcga gagcctgaac cagccaagta gcgtgaagga     420
tgactgccct atggttgta  aacttctttt ataaaggaat aaagtcgggt atggataccc     480
gtttgcatgt actttatgaa taaggatcgg ctaactccgt gccagcagcc gcggtaatac     540
ggaggatccg agcgttatcc ggatttattg ggtttaaagg gagcgtagat ggatgtttaa     600
gtcagttgtg aaagtttgcg gctcaaccgt aaaattgcag ttgatactgg atatcttgag     660
tgcagttgag gcaggcggaa ttcgtggtgt agcggtgaaa tgcttagata tcacgaagaa     720
ctccgattgc gaaggcagcc tgctaagctg caactgacat tgaggctcga aagtgtgggt     780
atcaaacagg attagatacc ctggtagtcc acacggtaaa cgatgaatac tcgctgtttg     840
cgatatactg caagcggcca agcgaaagcg ttaagtattc cacctgggga gtacgccggc     900
aacggtgaaa ctcaaaggaa ttgacgggggg cccgcacaag cggaggaaca tgtggtttaa     960
```

| | |
|---|---:|
| ttcgatgata cgcgaggaac cttacccggg cttaaattgc agatgaatta cggtgaaagc | 1020 |
| cgtaagccgc aaggcatctg tgaaggtgct gcatggttgt cgtcagctcg tgccgtgagg | 1080 |
| tgtcggctta agtgccataa cgagcgcaac ccttgttgtc agttactaac aggttccgct | 1140 |
| gaggactctg acaagactgc catcgtaaga tgtgaggaag gtggggatga cgtcaaatca | 1200 |
| gcacggccct tacgtccggg gctacacacg tgttacaatg ggggtacag agggccgcta | 1260 |
| ccacgcgagt ggatgccaat ccccaaaacc tctctcagtt cggactggag tctgcaaccc | 1320 |
| gactccacga agctggattc gctagtaatc gcgcatcagc cacggcgcgg tgaatacgtt | 1380 |
| cccgggcctt gtacacaccg cccgtcaagc catgggagcc gggggtacct gaagtgcgta | 1440 |
| accgcgagga gcgccctagg gtaaaactgg tgactggggc taagtcgtaa caaggtagcc | 1500 |
| gtaccggaag | 1510 |

<210> SEQ ID NO 2
<211> LENGTH: 1489
<212> TYPE: DNA
<213> ORGANISM: Bacteroides vulgatus

<400> SEQUENCE: 2

| | |
|---|---:|
| agagtttgat cctggctcag gatgaacgct agctacaggc ttaacacatg caagtcgagg | 60 |
| ggcagcatgg tcttagcttg ctaaggccga tggcgaccgg cgcacgggtg agtaacacgt | 120 |
| atccaacctg ccgtctactc ttggacagcc ttctgaaagg aagattaata caagatggca | 180 |
| tcatgagtcc gcatgttcac atgattaaag gtattccggt agacgatggg gatgcgttcc | 240 |
| attagatagt aggcggggta acggcccacc tagtcttcga tgggataggg ttctgagagg | 300 |
| aaggtccccc acattggaac tgagacacg tccaaactcc tacgggaggc agcagtgagg | 360 |
| aatattggtc aatgggcgag agcctgaacc agccaagtag cgtgaaggat gactgcccta | 420 |
| tgggttgtaa acttctttta taaaggaata aagtcgggta tggataccccg tttgcatgta | 480 |
| ctttatgaat aaggatcggc taactccgtg ccagcagccg cggtaatacg gaggatccga | 540 |
| gcgttatccg gatttattgg gtttaaaggg agcgtagatg gatgtttaag tcagttgtga | 600 |
| aagtttgcgg ctcaaccgta aaattgcagt tgatactgga tatcttgagt gcagttgagg | 660 |
| caggcggaat tcgtggtgta gcggtgaaat gcttagatat cacgaagaac tccgattgcg | 720 |
| aaggcagcct gctaagctgc aactgacatt gaggctcgaa agtgtgggta tcaaacagga | 780 |
| ttagataccc tggtagtcca cacggtaaac gatgaatact cgctgtttgc gatatacggc | 840 |
| aagcggccaa gcgaaagcgt taagtattcc acctggggag tacgccggca acggtgaaac | 900 |
| tcaaaggaat tgacgggggc ccgcacaagc ggaggaacat gtggtttaat tcgatgatac | 960 |
| gcgaggaacc ttacccgggc ttaaattgca gatgaattac ggtgaaagcc gtaagccgca | 1020 |
| aggcatctgt gaaggtgctg catggttgtc gtcagctcgt gccgtgaggt gtcggcttaa | 1080 |
| gtgccataac gagcgcaacc cttgttgtca gttactaaca ggttatgctg aggactctga | 1140 |
| caagactgcc atcgtaagat gtgaggaagg tgggatgac gtcaaatcag cacggccctt | 1200 |
| acgtccgggg ctacacacgt gttacaatgg ggggtacaga gggccgctac cacgcgagtg | 1260 |
| gatgccaatc cccaaaacct ctctcagttc ggactggagt ctgcaacccg actccacgaa | 1320 |
| gctggattcg ctagtaatcg cgcatcagcc acggcgcggt gaatacgttc ccgggccttg | 1380 |
| tacacaccgc ccgtcaagcc atgggagccg ggggtacctg aagtgcgtaa ccgcgaggag | 1440 |
| cgccctaggg taaaactggt gactgggget aagtcgtaac aaggtaacc | 1489 |

<210> SEQ ID NO 3
<211> LENGTH: 1493
<212> TYPE: DNA
<213> ORGANISM: Bacteroides dorei

<400> SEQUENCE: 3

| | |
|---|---|
| agagtttgat cctggctcag gatgaacgct agctacaggc ttaacacatg caagtcgagg | 60 |
| ggcagcatgg tcttagcttg ctaaggctga tggcgaccgg cgcacgggtg agtaacacgt | 120 |
| atccaacctg ccgtctactc ttggccagcc ttctgaaagg aagattaatc caggatggga | 180 |
| tcatgagttc acatgtccgc atgattaaag gtattttccg gtagacgatg gggatgcgtt | 240 |
| ccattagata gtaggcgggg taacggccca cctagtcaac gatggatagg ggttctgaga | 300 |
| ggaaggtccc ccacattgga actgagacac ggtccaaact cctacgggag gcagcagtga | 360 |
| ggaatattgg tcaatgggcg atggcctgaa ccagccaagt agcgtgaagg atgactgccc | 420 |
| tatgggttgt aaacttcttt tataaaggaa taaagtcggg tatgcatacc cgtttgcatg | 480 |
| tactttatga ataaggatcg gctaactccg tgccagcagc cgcggtaata cggaggatcc | 540 |
| gagcgttatc cggatttatt gggtttaaag ggagcgtaga tggatgttta agtcagttgt | 600 |
| gaaagtttgc ggctcaaccg taaaattgca gttgatactg gatgtcttga gtgcagttga | 660 |
| ggcaggcgga attcgtggtg tagcggtgaa atgcttagat atcacgaaga actccgattg | 720 |
| cgaaggcagc ctgctaagct gcaactgaca ttgaggctcg aaagtgtggg tatcaaacag | 780 |
| gattagatac cctggtagtc cacacggtaa acgatgaata ctcgctgttt gcgatatacg | 840 |
| gcaagcggcc aagcgaaagc gttaagtatt ccacctgggg agtacgccgg caacggtgaa | 900 |
| actcaaagga attgacgggg gcccgcacaa gcggaggaac atgtggttta attcgatgat | 960 |
| acgcgaggaa ccttacccgg gcttaaattg cactcgaatg atccggaaac ggttcagcta | 1020 |
| gcaatagcga gtgtgaaggt gctgcatggt tgtcgtcagc tcgtgccgtg aggtgtcggc | 1080 |
| ttaagtgcca taacgagcgc aaccctttgtt gtcagttact aacaggtgat gctgaggact | 1140 |
| ctgacaagac tgccatcgta agatgtgagg aaggtgggga tgacgtcaaa tcagcacggc | 1200 |
| ccttacgtcc ggggctacac acgtgttaca atggggggta cagagggccg ctaccacgcg | 1260 |
| agtggatgcc aatccctaaa acccctctca gttcggactg gagtctgcaa cccgactcca | 1320 |
| cgaagctgga ttcgctagta atcgcgcatc agccacggcg cggtgaatac gttcccgggc | 1380 |
| cttgtacaca ccgcccgtca agccatggga gccggggta cctgaagtgc gtaaccgcga | 1440 |
| ggatcgccct agggtaaaac tggtgactgg ggctaagtct aaccaaggta acc | 1493 |

<210> SEQ ID NO 4
<211> LENGTH: 1490
<212> TYPE: DNA
<213> ORGANISM: Bacteroides dorei

<400> SEQUENCE: 4

| | |
|---|---|
| agagtttgat cctggctcag gatgaacgct agctacaggc ttaacacatg caagtcgagg | 60 |
| ggcagcatgg tcttagcttg ctaaggctga tggcgaccgg cgcacgggtg agtaacacgt | 120 |
| atccaacctg ccgtctactc ttggccagcc ttctgaaagg aagattaatc caggatggga | 180 |
| tcatgagttc acatgtccgc atgattaaag gtattttccg gtagacgatg gggatgcgtt | 240 |
| ccattagata gtaggcgggg taacggccca cctagtcaac gatggatagg ggttctgaga | 300 |
| ggaaggtccc ccacattgga actgagacac ggtccaaact cctacgggag gcagcagtga | 360 |
| ggaatattgg tcaatgggcg atggcctgaa ccagccaagt agcgtgaagg atgactgccc | 420 |

```
tatgggttgt aaacttcttt tataaaggaa taaagtcggg tatgcatacc cgtttgcatg    480
tactttatga ataaggatcg gctaactccg tgccagcagc cgcggtaata cggaggatcc    540
gagcgttatc cggatttatt gggtttaaag ggagcgtaga tggatgttta agtcagttgt    600
gaaagtttgc ggctcaaccg taaaattgca gttgatactg gatgtcttga gtgcagttga    660
ggcaggcgga attcgtggtg tagcggtgaa atgcttagat atcacgaaga actccgattg    720
cgaaggcagc ctgctaagct gcaactgaca ttgaggctcg aaagtgtggg tatcaaacag    780
gattagatac cctggtagtc cacacggtaa acgatgaata ctcgctgttt gcgatatacg    840
gcaagcggcc aagcgaaagc gttaagtatt ccacctgggg agtacgccgg caacggtgaa    900
actcaaagga attgacgggg gcccgcacaa gcggaggaac atgtggttta attcgatgat    960
acgcgaggaa ccttacccgg gcttaaattg cactcgaatg atccggaaac ggttcagcta   1020
gcaatagcga gtgtgaaggt gctgcatggt tgtcgtcagc tcgtgccgtg aggtgtcggc   1080
ttaagtgcaa cgagcgcaac ccttgttgtc agttactaac aggtgatgct gaggactctg   1140
acaagactgc catcgtaaga tgtgaggaag gtggggatga cgtcaaatca gcacggccct   1200
tacgtccggg gctacacacg tgttacaatg ggggtacag agggccgcta ccacgcgagt    1260
ggatgccaat ccctaaaacc cctctcagtt cggactggag tctgcaaccc gactccacga   1320
agctggattc gctagtaatc gcgcatcagc cacggcgcgg tgaatacgtt cccgggcctt   1380
gtacacaccg cccgtcaagc catgggagcc gggggtacct gaagtgcgta accgcgagga   1440
tcgccctagg gtaaaactgg tgactggggc taagtcgtaa caaggtaacc              1490

<210> SEQ ID NO 5
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 5
gcatccacgt gttggctca                                                  19

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 6
ctccagccta ctcattggga tca                                             23

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 7
ccgagagtgc tgcctggatt a                                               21

<210> SEQ ID NO 8
<211> LENGTH: 21
<212> TYPE: DNA
<213> ORGANISM: Artificial Sequence
<220> FEATURE:
```

<223> OTHER INFORMATION: Synthetic Oligonucleotide Primer

<400> SEQUENCE: 8
agcttgccct ggacagtcag a                                            21

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 9
ccaacttgca gctgtccatc tc                                           22

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 10
catcactgcc ttgggtccag                                              20

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 11
ggtggtggct ctccttgtca tt                                           22

<210> SEQ ID NO 12
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 12
acaccgactc gtacagggtg tagtc                                        25

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 13
agacgtgcca gtcagcatca ac                                           22

<210> SEQ ID NO 14
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 14
ctattccgat agcattgggt gagtg                                        25

```
<210> SEQ ID NO 15
<211> LENGTH: 24
<212> TYPE: DNA
<213> ORGANISM: Artificial Sequence
<220> FEATURE:
<223> OTHER INFORMATION: Synthetic Oligonucleotide Primer

<400> SEQUENCE: 15
agtttccatg tccaaggctc attc                                           24

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 16
ttgtaacggc aaggcagcaa ta                                             22

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 17
tggcatatga ccgttgtgtg tg                                             22

<210> SEQ ID NO 18
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 18
acgtttgagc agatggaaac tcttg                                          25

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 19
tctacgaggg actgtggatg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 20
tcagattcag caaggagtcg                                                20

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide Primer
```

```
<400> SEQUENCE: 21
ctttggctat gggcttccag tc                                          22

<210> SEQ ID NO 22
<211> LENGTH: 24
<212> TYPE: DNA
<213> ORGANISM: Artificial Sequence
<220> FEATURE:
<223> OTHER INFORMATION: Synthetic Oligonucleotide Primer

<400> SEQUENCE: 22
gcaaggagga cagagtttat cgtg                                        24

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 23
ctcatgatag tgcctgtgtc ctcaa                                       25

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 24
agggccagca taggtgcaag                                             20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 25
tgtgtccgtc gtggatctga                                             20

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 26
ttgctgttga agtcgcagga g                                           21

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 27
tgaacgggaa gctcactgg                                              19

<210> SEQ ID NO 28
<211> LENGTH: 20
```

```
<212> TYPE: DNA
<213> ORGANISM: Artificial Sequence
<220> FEATURE:
<223> OTHER INFORMATION: Synthetic Oligonucleotide Primer

<400> SEQUENCE: 28
tccaccaccc tgttgctgta                                            20

<210> SEQ ID NO 29
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 29
caattcacac tgaatgccag ctc                                        23

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 30
caagcagtcc gtctcgtcca                                            20

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 31
tccaggatga ggacatgagc ac                                         22

<210> SEQ ID NO 32
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 32
gaacgtcaca caccagcagg tta                                        23

<210> SEQ ID NO 33
<211> LENGTH: 24
<212> TYPE: DNA
<213> ORGANISM: Artificial Sequence
<220> FEATURE:
<223> OTHER INFORMATION: Synthetic Oligonucleotide Primer

<400> SEQUENCE: 33
ccacttcaca agtcggaggc ttta                                       24

<210> SEQ ID NO 34
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 34
```

```
gcaagtgcat catcgttgtt catac                                          25

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 35
acgcgcaaac atgagtccag                                                20

<210> SEQ ID NO 36
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 36
ctcagcagca gcaacagcat c                                              21

<210> SEQ ID NO 37
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 37
atgtccggcc gatgctctc                                                 19

<210> SEQ ID NO 38
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 38
tttggctgct cttgggtctg tat                                            23

<210> SEQ ID NO 39
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 39
gggcctaaac ccagtctgtt tg                                             22

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 40
gcccggtaag gtccatgcta                                                20

<210> SEQ ID NO 41
<211> LENGTH: 20
<212> TYPE: DNA
<213> ORGANISM: Artificial Sequence
```

```
<220> FEATURE:
<223> OTHER INFORMATION: Synthetic Oligonucleotide Primer

<400> SEQUENCE: 41
aaactggtcg ggcaattctg                                              20

<210> SEQ ID NO 42
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 42
agggttggac acctgaatgc ta                                           22

<210> SEQ ID NO 43
<211> LENGTH: 16
<212> TYPE: DNA
<213> ORGANISM: Artificial Sequence
<220> FEATURE:
<223> OTHER INFORMATION: Synthetic Oligonucleotide Primer

<400> SEQUENCE: 43
ctacgggggg cagcag                                                  16

<210> SEQ ID NO 44
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 44
ggactaccgg ggtatct                                                 17

<210> SEQ ID NO 45
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 45
tgccggcata tacgagtgtg a                                            21

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 46
cccgatggca ggtattacca ag                                           22

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 47
tttttgacag ggggagtgg                                               19
```

```
<210> SEQ ID NO 48
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 48
tgctgcagag gtcaaagttc aag                                            23

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 49
gaatgatggt tggtatggtg cg                                             22

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 50
tcagaagtgt gtctactgtc cg                                             22

<210> SEQ ID NO 51
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 51
ctacgggggg cagcag                                                    16

<210> SEQ ID NO 52
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 52 agatacccccg gtagtcc                                                  17
```

LIPOPOLYSACCHARIDE-REGULATED ENTERIC BACTERIA AND USE THEREOF

CROSS REFERENCE TO RELATED APPLICATIONS

This application is a National Stage of International Application No. PCT/JP2019/004763 filed Feb. 8, 2019, claiming priority based on Japanese Patent Application No. 2018-022578 filed Feb. 9, 2018.

TECHNICAL FIELD

The present invention relates to a lipopolysaccharide (hereinafter sometimes to be abbreviated as "LPS")-regulated enteric bacterium and use thereof. More particularly, the present invention relates to a combination of two species of the particular bacteria belonging to the genus *Bacteroides* (namely, *Bacteroides vulgatus* and *Bacteroides dorei*) that can control LPS production by enteric bacteria and transfer thereof into the blood, a medicament, food, or the like containing the combination, particularly an agent for preventing and/or improving diseases involving LPS (e.g., circulatory diseases, inflammatory diseases, and metabolic diseases), a method for diagnosing the above-mentioned diseases which uses the abundance of the bacteria in the intestinal microflora as an index, and the like.

BACKGROUND ART

Advances in understanding of intestinal microflora and its role in host metabolism and immunity have led to unprecedented interest in developing a diagnostic and therapeutic target, which relates to the intestinal microflora, for many diseases. The spread of next-generation sequencing technology and multiomics analysis has dramatically expanded our knowledge relating to the microbial world. The evidence is increasing in number, which suggests a strong relationship between intestinal microflora and cardiovascular disease. For example, trimethylamine (TMA) and trimethylamine-N-oxide (TMAO), which are metabolites of the dietary phosphatidylcholine by intestinal microflora, are known to be associated with the process of cardiovascular disease, particularly arteriosclerosis.

However, recent clinical tests have shown that ingestion of fish dramatically, though temporarily, increases blood TMAO levels. It contradicts the above and reveals the limitation of the current understanding in the field as to the relationship between diet and intestinal microflora.

The genus *Bacteroides* (*Bacteroides*) contains some enteric bacteria that are predominantly found in humans and is known to play an important role in maintaining a healthy intestinal ecosystem. Individuals classified as enterotype 3, which is characterized by low levels of the genus *Bacteroides*, have a high incidence of symptomatic arteriosclerosis (non-patent document 1). Furthermore, it has been clarified that the abundance of the genus *Bacteroides* decreases in patients with arteriosclerotic ischemic cerebral infarction or transient cerebral ischemic attack (non-patent document 2). Consistent with these observations, previous studies by the present inventors using terminal-restriction fragment length polymorphism (T-RFLP) analysis have confirmed that the abundance of *Bacteroides* is lower in patients with coronary artery disease (CAD) than in patients with risk factors of atherosclerosis but without atherosclerotic disease and in healthy volunteers (non-patent documents 3, 4). Furthermore, metagenomic analysis of enteric bacteria with shotgun sequencing has shown a decrease in *Bacteroides* species in CAD patients as well (non-patent document 5). These findings strongly suggest a relationship between the genus *Bacteroides* and CAD.

However, it remains unclear which particular *Bacteroides* species are involved and what their true role is in CAD.

Lipopolysaccharide (LPS), which is a component of the cell wall outer membrane of Gram-negative bacteria, is known to activate immunocytes such as macrophage and metabolic endotoxemia has been shown to be involved in chronic inflammation and cardiovascular-metabolic diseases such as diabetes and arteriosclerosis (non-patent document 6). The present inventors previously found that aseptic ApoE-deficient mice show suppression of formation of atherosclerotic lesion in the aortic sinuses and concomitantly low levels of LPS in the blood and inflammatory cytokine in macrophages and aortas compared to the same mice raised under conventional conditions (non-patent document 7).

On the other hand, patent document 1 discloses a capsule composition for oral administration containing components (e.g., LPS) derived from three species of the genus *Bacteroides*, including *Bacteroides vulgatus*, and describes that it can be used for treating and delaying the onset of various inflammatory diseases, autoimmune diseases, and the like. However, it has not been demonstrated that the composition actually has the efficacy.

In addition, non-patent document 8 describes that LPS derived from *Bacteroides dorei* is structurally different from LPS from *Escherichia coli* and has a weaker Toll-like receptor 4 (TLR4) stimulating ability and does not easily induce innate immunity.

However, there is no report that the bacteria of the genus *Bacteroides* affect the whole LPS production in the intestine, including by other enteric bacteria.

DOCUMENT LIST

Patent Document patent document 1: National Publication of International Patent Application No. 2013-527240

Non-Patent Documents non-patent document 1: Karlsson, F. H. et al. Nat Commun. 3, 1245 (2012).
non-patent document 2: Yin, J. et al. J Am Heart Assoc. 4, E002699 (2015).
non-patent document 3: Emoto, T. et al. J Atheroscler Thromb. 23, 908-921 (2016).
non-patent document 4: Emoto, T. et al. Heart Vessels. 32, 39-46 (2017).
non-patent document 5: Jie, Z. et al. Nat Commun. 18, 845 (2017).
non-patent document 6: Patel, P. N. et al. Arterioscler. Thromb. Vasc. Biol. 35, 525-534 (2015).
non-patent document 7: Kasahara, K. et al. J Lipid Res. 58, 519-528 (2017).
non-patent document 8: Vatanen, T. et al. Cell. 165, 842-853 (2016).

SUMMARY OF INVENTION

Technical Problem

Despite the widespread of statin therapy over the last 10 years, CAD remains one of the leading causes of death around the world. The present invention aims to identify the specific bacterial species of the intestinal microflora that can be the target of a novel and inexpensive prophylactic and/or therapeutic strategy for CAD.

Solution to Problem

To achieve the above-mentioned purposes, the present inventors first performed 16S ribosomal RNA (rRNA) gene random sequencing and compared the intestinal microflora in CAD patients and non-CAD patients. As a result, they have found that *Bacteroides vulgatus* and *Bacteroides dorei* decreased in the CAD patients. Furthermore, by a series of analyses in ApoE-deficient mice with a tendency for arteriosclerosis, the present inventors have elucidated the action mechanism underlying the link between these *Bacteroides* species and arteriosclerosis. That is, they have found that these *Bacteroides* species significantly suppress the LPS production by enteric bacteria, reduce the permeability of intestinal barrier by strengthening the tight junctions of the barrier, and inhibit the transfer of LPS into the blood (i.e., induction of endotoxemia), thereby suppressing the inflammation-induced immune response and inhibiting the formation of arteriosclerosis lesions.

The present inventors have conducted further studies based on these findings and concluded that the ingestion of *Bacteroides vulgatus* and *Bacteroides dorei* is useful for the prophylaxis and/or improvement of circulatory diseases including arteriosclerosis, inflammatory diseases, and metabolic diseases and that the aforementioned diseases can be diagnosed using the abundance of the *Bacteroides* species in intestinal microflora as an index, which has resulted in the completion of the present invention.

Namely, the present invention provides the following.
[1] A combination comprising
(1) a composition comprising a live bacterium *of Bacteroides vulgatus* isolated from nature, and
(2) a composition comprising a live bacterium of *Bacteroides dorei* isolated from nature.
[2] The combination of [1], wherein the composition of the aforementioned (1) and the composition of the aforementioned
(2) are one and the same composition.
[3] The combination of [1] or [2], wherein the combination is a pharmaceutical product or a pharmaceutical additive.
[4] The combination of [1] or [2], wherein the combination is a food or a feed, or an additive therefor.
[5] The combination of any of [1] to [4], wherein the combination is for preventing and/or improving a disease related to an elevated blood or intestinal lipopolysaccharide level.
[6] The combination of [5], wherein the aforementioned disease is a circulatory disease, an inflammatory disease, or a metabolic disease.
[7] The combination of [5], wherein the aforementioned disease is a circulatory inflammatory disease selected from the group consisting of atrial fibrillation, cardiac failure, an ischemic cardiac disease, myocardial infarction, angina pectoris, hypertension, arteriosclerosis, aneurysm of aorta, aortic dissection, arteriosclerosis obliterans, and aortic stenosis.
[8] The combination of [5], wherein the aforementioned disease is an inflammatory disease selected from the group consisting of hepatitis, non-alcoholic steatohepatitis, fatty liver, liver cancer, intestinal inflammation, irritable bowel syndrome, gastritis, collagen disease, chronic rheumatoid arthritis; chronic nephritis, IgA nephropathy, bronchial asthma, interstitial pneumonia, a drug-induced lung disorder, pulmonary infiltration with eosinophilia syndrome, atypical mycobacteriosis, allergic rhinitis, atopic dermatitis, and sepsis.
[9] The combination of [5], wherein the aforementioned disease is a metabolic disease selected from the group consisting of diabetes, obesity, metabolic syndrome, a lifestyle-related disease, dyslipidemia and osteoporosis.
[10] A method for preventing and/or improving a disease related to an elevated blood or intestinal lipopolysaccharide level, the method comprising oral ingestion of a live bacterium of *Bacteroides vulgatus* isolated from nature and a live bacterium of *Bacteroides dorei* isolated from nature.
[11] The method of [10], wherein the aforementioned disease is a circulatory disease, an inflammatory disease, or a metabolic disease.
[12] A method for testing for a disease related to an elevated blood or intestinal lipopolysaccharide level, the method comprising measuring an abundance of *Bacteroides vulgatus* and *Bacteroides dorei* in the intestinal microflora of a test subject.
[13] The method of [12], wherein the aforementioned disease is a circulatory disease, an inflammatory disease, or a metabolic disease.
[14] The method of [12] or [13], wherein
(1) 16S rRNA gene comprising a nucleotide sequence having an identity of not less than 98% with the nucleotide sequence shown in SEQ ID NO: 1 or 2, and
(2) 16S rRNA gene comprising a nucleotide sequence having an identity of not less than 98% with the nucleotide sequence shown in SEQ ID NO: 3 or 4 are detected.
[15] A reagent for testing risks of developing a disease related to an elevated blood or intestinal lipopolysaccharide level, the reagent comprising primer sets or probes capable of detecting 16S rRNA genes of *Bacteroides vulgates* and *Bacteroides dorei*.
[16] The reagent of [15], wherein the aforementioned disease is a circulatory disease, an inflammatory disease, or a metabolic disease.
[17] The reagent of [15] or [16], wherein the 16S rRNA genes comprise
(1) a nucleotide sequence having an identity of not less than 98% with the nucleotide sequence shown in SEQ ID NO: 1 or 2, and
(2) a nucleotide sequence having an identity of not less than 98% with the nucleotide sequence shown in SEQ ID NO: 3 or 4.

Advantageous Effects of Invention

According to the present invention, the prophylaxis and/or improvement of circulatory diseases including arteriosclerosis, diseases with chronic inflammation and metabolic diseases with metabolic abnormalities such as glycolipid metabolism become(s) possible through oral ingestion of the microorganisms that can be fermentatively produced in large amounts (probiotics). Thus, it provides an inexpensive and simple control strategy for those diseases and contributes to the medical economy in an aging society. According to the present invention, diagnosis and risk prediction for the onset of the aforementioned diseases also be possible through the analysis of the microbiome in feces, and a non-invasive clinical test method is provided.

The V3-V4 region of the bacterial 16S rRNA was sequenced in fecal samples from 30 control patients (who did not develop CAD but had coronary risk factors) and 30 CAD patients. (a) Participants were classified into three clusters based on the abundance of genus in the intestinal microflora. (b) The distribution of each major genus between clusters. One-way ANOVA was used to compare the distribution between clusters in each genus. (c) The distribution of the control and the CAD patients in each cluster. $\chi^2$ test was executed to compare the three clusters. (d) The relative abundance (the percentage to total intestinal microflora) of the genus *Bacteroides* in the control and CAD patients. (e) The relative abundance (the percentage to total genus *Bacteroides*) of *Bacteroides* species in the control and CAD patients. (f) The relative abundance (the percentage of to total intestinal microflora) of *Bacteroides vulgatus* and *Bacteroides dorei*. *P<0.05, P<0.01, *P<0.001. To determine statistical significance, Mann-Whitney U test was used (b, d, f). The data shows median value±the interquartile range (range from first to third quartile) (b, d, f).

Figure 2:
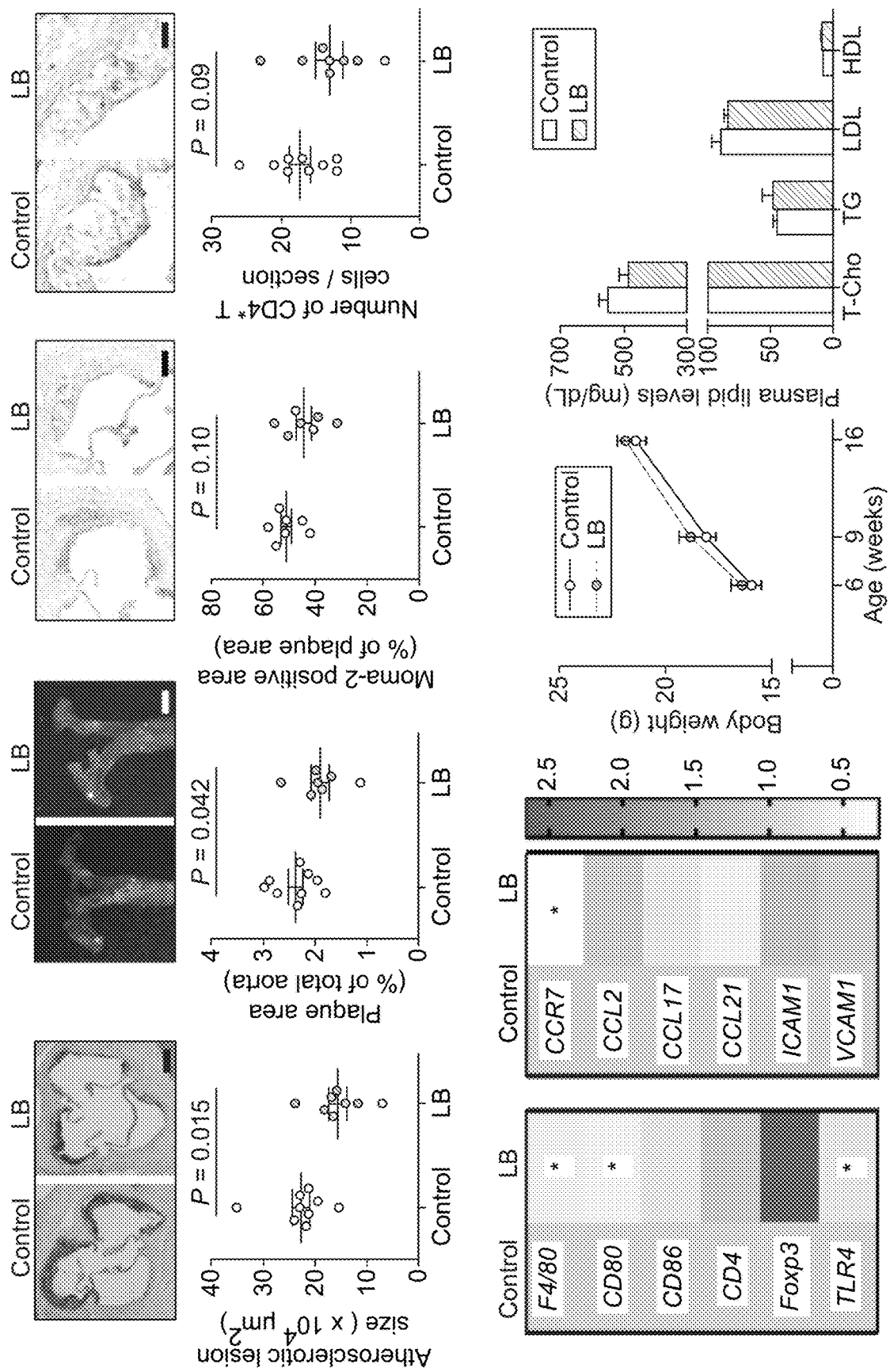

FIG. 2 shows the effect of the gavage with live *Bacteroides vulgatus* and *Bacteroides dorei* on the development of atherosclerosis and plaque inflammation.

Six-week-old female Apoe$^{-/-}$ mice treated with live *Bacteroides vulgatus* ATCC 8482$^T$ strain and *Bacteroides dorei* DSM 17855$^T$ strain, or vehicle (control) were sacrificed at 16 weeks of age and atherosclerotic lesions were evaluated. (a) Representative micrographs and quantitative analysis of oil red O staining of lesion regions due to atherosclerosis in aortic sinus (8-9 samples per group). The black bar shows 200 µm. (b) Representative micrographs and quantitative analysis of oil red O staining of the atherosclerotic plaque region of the aorta (7-9 samples per group). The white bar shows 1.5 mm. (c) Representative fluorescent staining of macrophage and quantitative analysis of MOMA-2 positive staining in aortic sinus (7 samples per group). The black bar shows 100 µm. (d) Representative section and quantitative analysis of CD4$^+$ T cells in aortic sinus (8-9 samples per group). The black bar shows 50 µm. (e) The mRNA level in atherosclerotic aorta. The data was normalized to the housekeeping GAPDH gene and is shown as mean (4-5 samples per group). (f) The changes in body weight throughout the experiment period (8-9 samples per group). (g) The comparison of plasma lipid profiles (8-9 samples per group). LB: Treated with live *Bacteroides vulgatus* ATCC 8482$^T$ strain and *Bacteroides dorei* DSM 17855$^T$ strain; T-Cho: total cholesterol; TG: triglyceride; LDL: low density lipoprotein cholesterol; HDL: high density lipoprotein cholesterol. *P<0.05, 2-tailed Student's t-test. The data represents mean±standard error of the mean.

Figure 3:
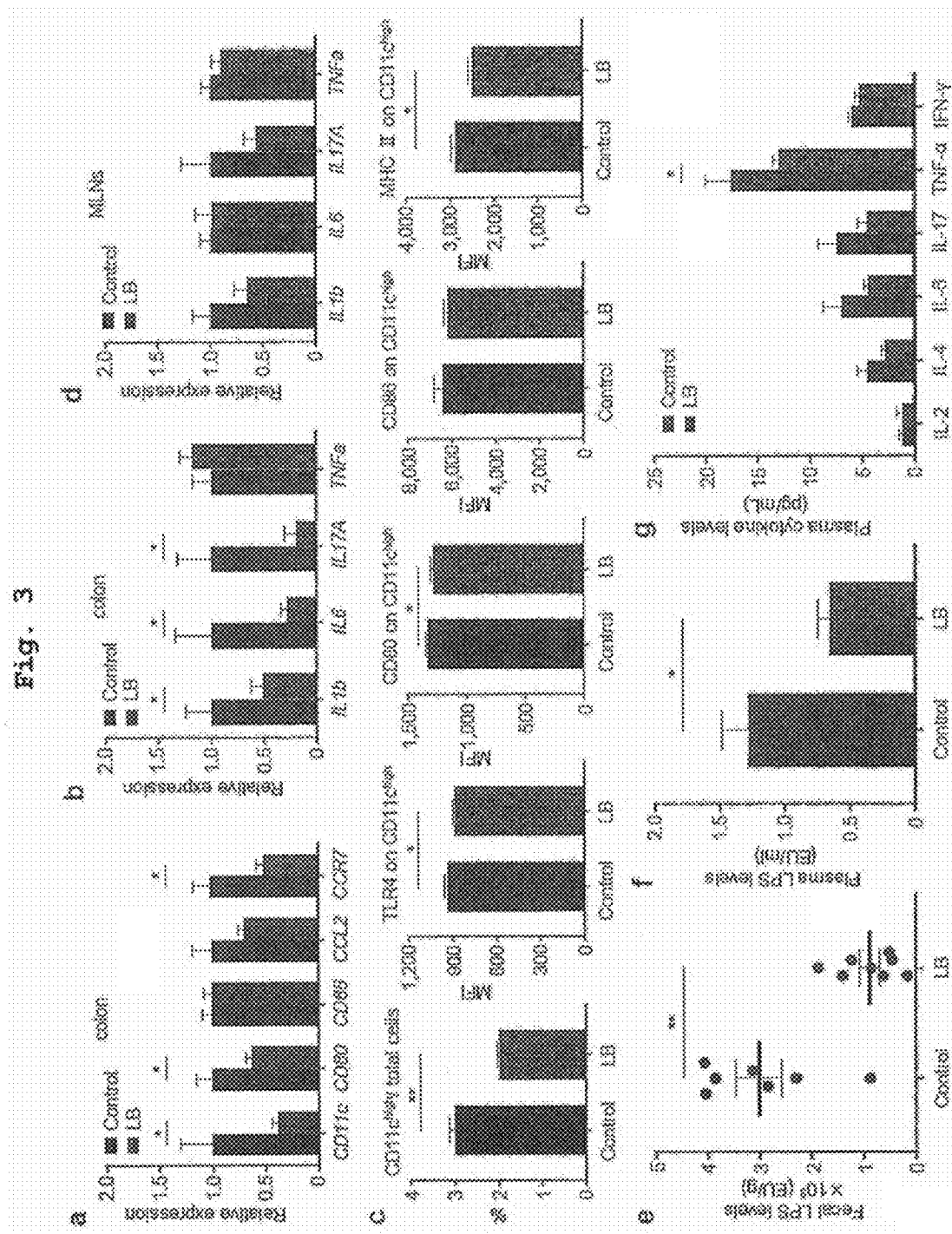

FIG. 3 shows the changes in intestinal immune response and the production of lipopolysaccharide (LPS) by intestinal microorganisms.

The colon and mesentery lymph node (MLNs) were excised from 16-week-old female Apoe$^{-/-}$ mice treated with *Bacteroides vulgatus* ATCC 8482$^T$ strain and *Bacteroides dorei* DSM 17855$^T$ strain or a vehicle (control). (a) mRNA expression levels of immunocyte markers and chemokine/chemokine receptors in colon (7-8 samples per group). (b) mRNA expression levels of the pro-inflammatory cytokines in colon (7-8 samples per group). (c) Flow cytometry analysis of the specific cell markers in MLN (4-5 samples per group). (d) mRNA expression levels of the cytokines in MLN (5 samples per group). (e) The quantification of fecal LPS levels by limulus amebocyte lysate assay (7-8 samples per group). (f) The quantification of plasma LPS levels by limulus amebocyte lysate assay (5 samples per group). (g) The quantification of plasma cytokine levels by cytokine bead array (4-5 samples per group). LB: treated with live *Bacteroides vulgatus* ATCC 8482$^T$ strain and *Bacteroides dorei* DSM 17855$^T$ strain; MFI: mean fluorescence intensity. To detect a significant difference between the two groups, 2-tailed Student's t-test was used. The data represents mean±standard error of the mean (a-g). *P<0.05, **P<0.01.

Figure 4:
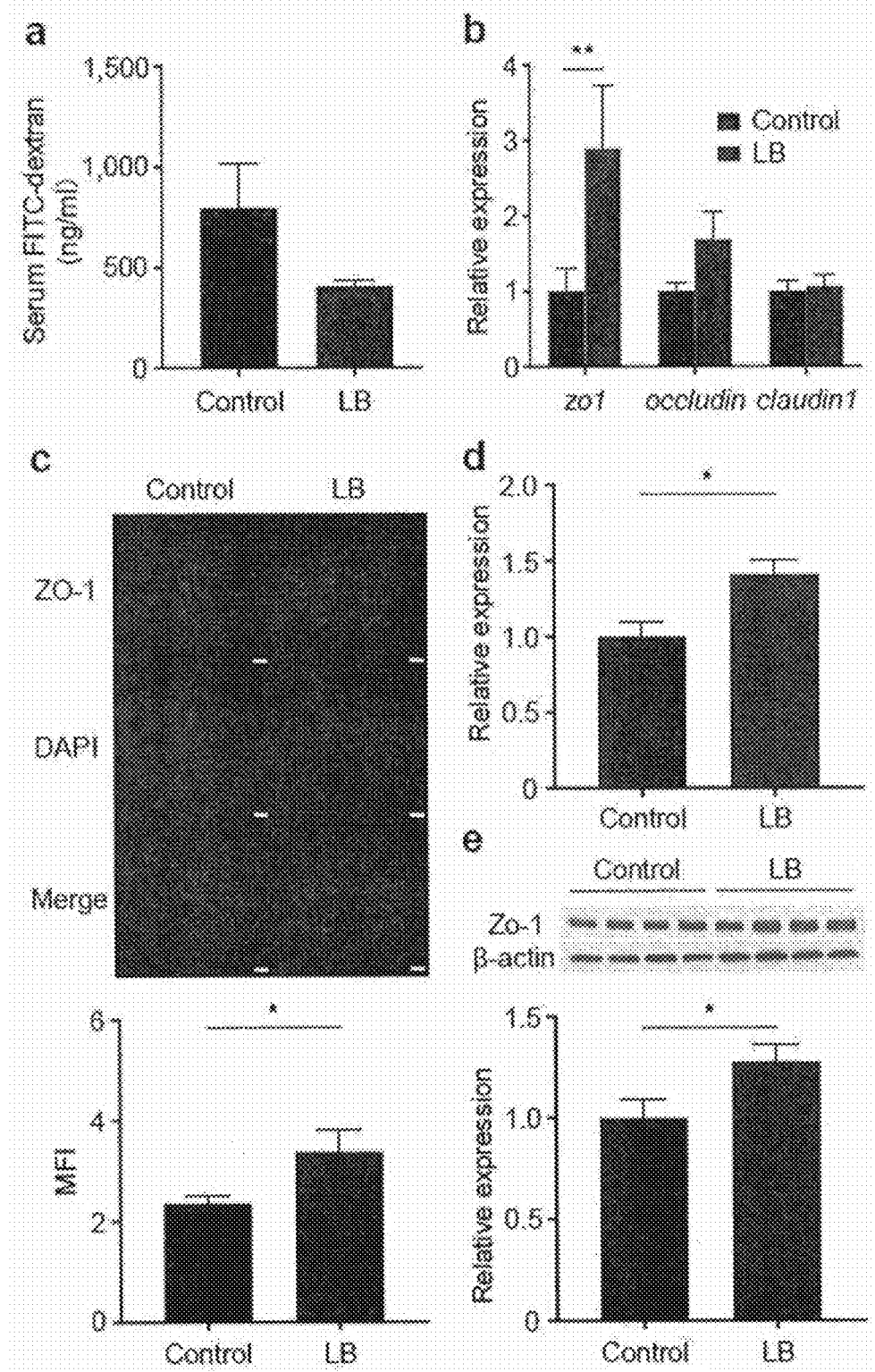

FIG. 4 shows the effect of live *Bacteroides* treatment on tight junction formation.

(a) The measurement of the fluorescein isothiocyanate (FITC)-labeled dextran concentration of serum at 4 hr after oral gavage for mice (4-5 samples per group). (b) The mRNA expression levels of the tight junction genes in mouse colon (7-8 samples per group). (c) The tight junction protein ZO-1 visualized by immunofluorescence staining (4-5 samples per group). The white bar shows 250 µm. (d) The mRNA level of the tight junction gene in HT29 cells stimulated with fecal supernatant (5 samples per group). (e) Western blot analysis of ZO-1 expression in HT29 cells stimulated with fecal supernatant (normalized to β actin) (8 samples per group). LB: treated with live *Bacteroides vulgatus* ATCC 8482$^T$ strain and *Bacteroides dorei* DSM 17855$^T$ strain; LPS: lipopolysaccharide; MFI: mean fluorescence intensity. *P<0.05, **P<0.01, 2-tailed Student's t-test. The data represents mean±standard error the mean.

Figure 5:
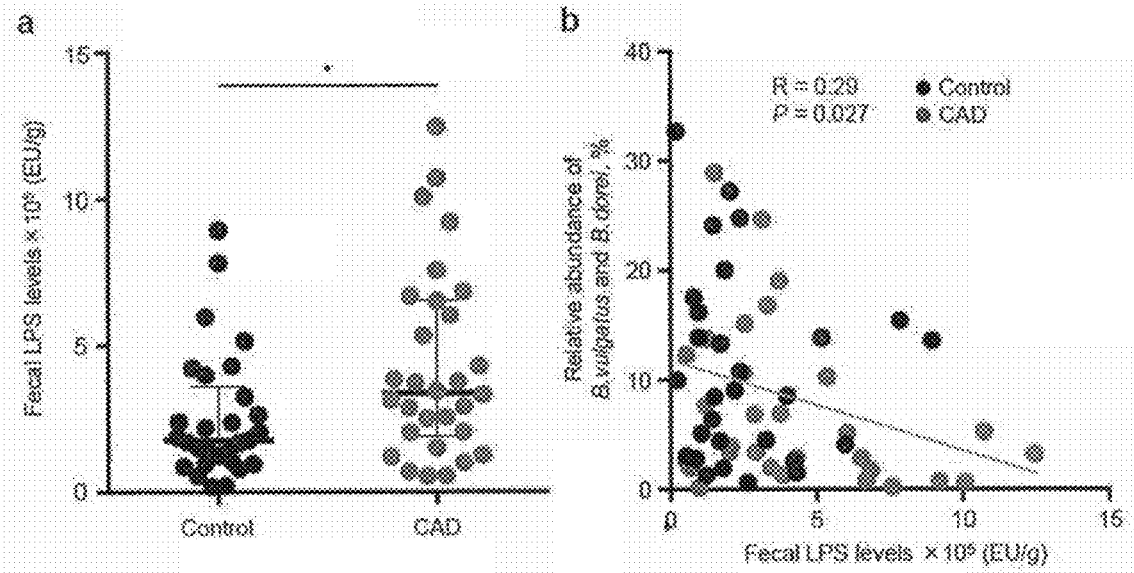

FIG. 5 shows intestinal microbial LPS production in patients with or without CAD.

Figure 6:
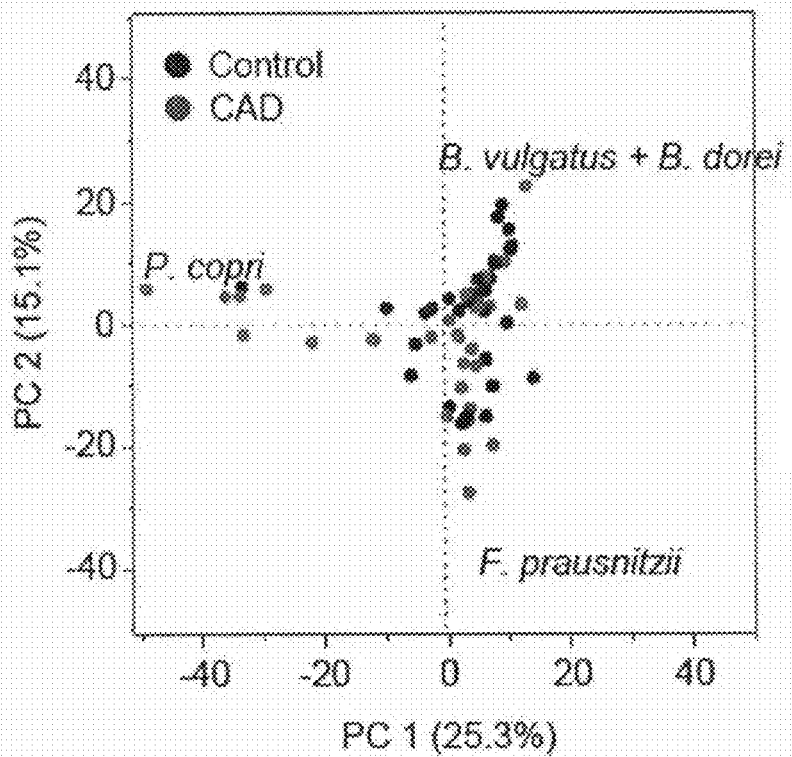

(a) The fecal LPS level was quantified by limulus amebocyte lysate assay in the same sample as that used for 16S rRNA gene sequencing (29-30 samples per group). To determine significance, 2-tailed Student's t-test was used. *P<0.05. The data represents median value±the interquartile range (range from first to third quartile). (b) A simple linear correlation was calculated by determining the Pearson's correlation coefficient for the statistical correlation between fecal LPS levels and the relative abundance of *Bacteroides vulgatus* and *Bacteroides dorei*, (59 samples; 29 controls and 30 CADs). CAD: coronary heart disease patients FIG. 6 shows intestinal microflora profiles in CAD patients or non-CAD patients. To compare the distribution of intestinal microbiota, the principal component analysis was performed at the species level. The species are shown in the figure, which have larger contribution in the principal component than other.

Figure 7:
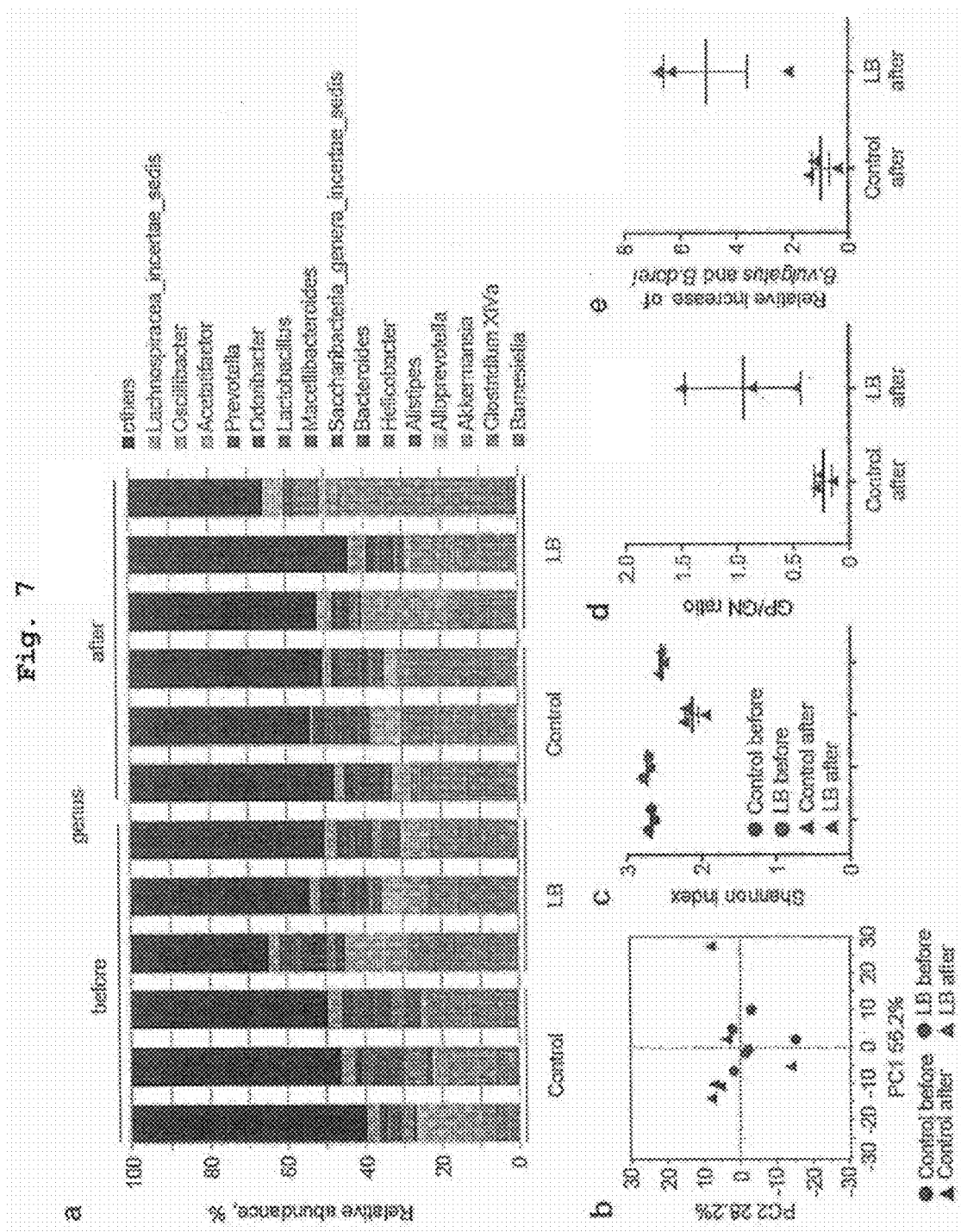

FIG. 7 shows the effect of gavage with live *Bacteroides vulgatus* and *Bacteroides dorei* on the intestinal microflora of a mouse with tendency of atherosclerosis. Feces were collected from the female Apoe$^{-/-}$ mice, which ingested, for 10 weeks, a general feed, and a feed treated with live *Bacteroides vulgatus* ATCC 8482$^T$ strain and *Bacteroides dorei* DSM 17855$^T$ strain or a vehicle. The V3-V4 region of the bacterial 16S rRNA was sequenced. (a) The relative abundance of the 15 most abundant genera of microorganisms before and after treatment. (b) Principal component analysis (PCA) score plot at genus level. (c) Diversity of intestinal microorganisms determined from the viewpoint of Shannon-Wiener index. (d) The ratio of Gram-positive strain to Gram-negative strain after treatment. (e) Relative increases in the fecal abundance of *Bacteroides vulgatus* and *Bacteroides dorei* DNA after treatment (n=3 per group). LB: gavage with live *Bacteroides vulgatus* ATCC 8482$^T$ strain and *Bacteroides dorei* DSM 17855$^T$ strain; before: before experiment; after: 10 weeks after gavage.

Figure 8:
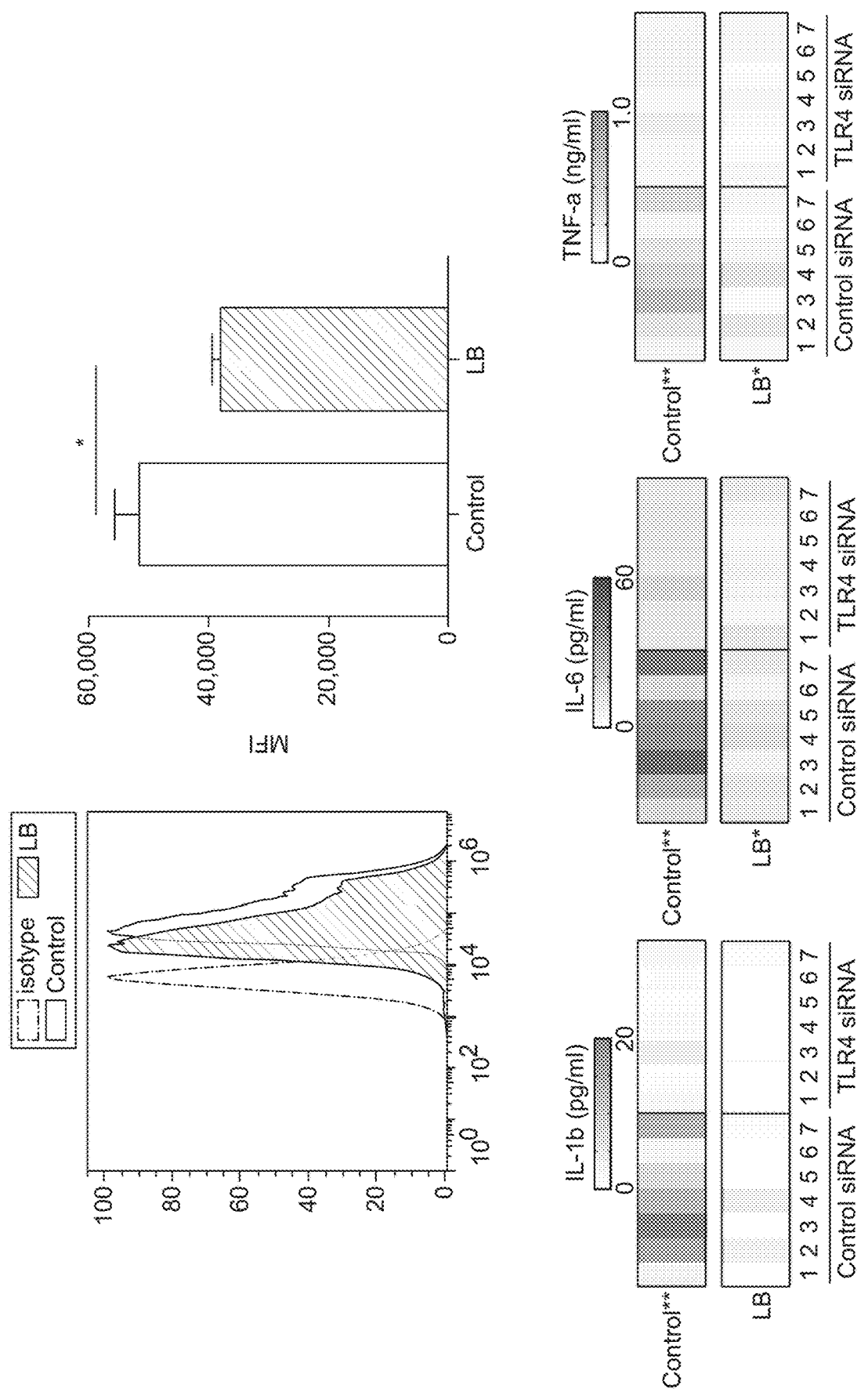

FIG. 8 shows the inhibition of cell proliferation and cytokine production by in vitro stimulation with mice fecal supernatant. RAW264.7 cells were stimulated with a fecal supernatant derived from mice treated for 10 weeks with live *Bacteroides vulgatus* ATCC 8482$^T$ strain and *Bacteroides dorei* DSM 17855$^T$ strain, or a vehicle (control). (a) Representative flow cytometric histogram (left panel) and quantitative analysis of Ki-67 expression (right panel) (5 samples per group). (b) RAW264.7 cells transfected with control siRNA or TLR4 siRNA were stimulated with fecal supernatant derived from each group of mice. The cytokine level was quantified by cytokine bead array (7 samples per group). LB: treated with live *Bacteroides vulgatus* ATCC 8482$^T$ strain and *Bacteroides dorei* DSM 17855$^T$ strain; MFI: mean fluorescence intensity. To detect a significant difference between two groups, 2-tailed Student's t-test (a) or Mann-Whitney U test (b) was used. The data shows mean±standard error of the mean (a), or median value±the interquartile range (range from first to third quartile) (b). *P<0.05, **P<0.01.

Figure 9:
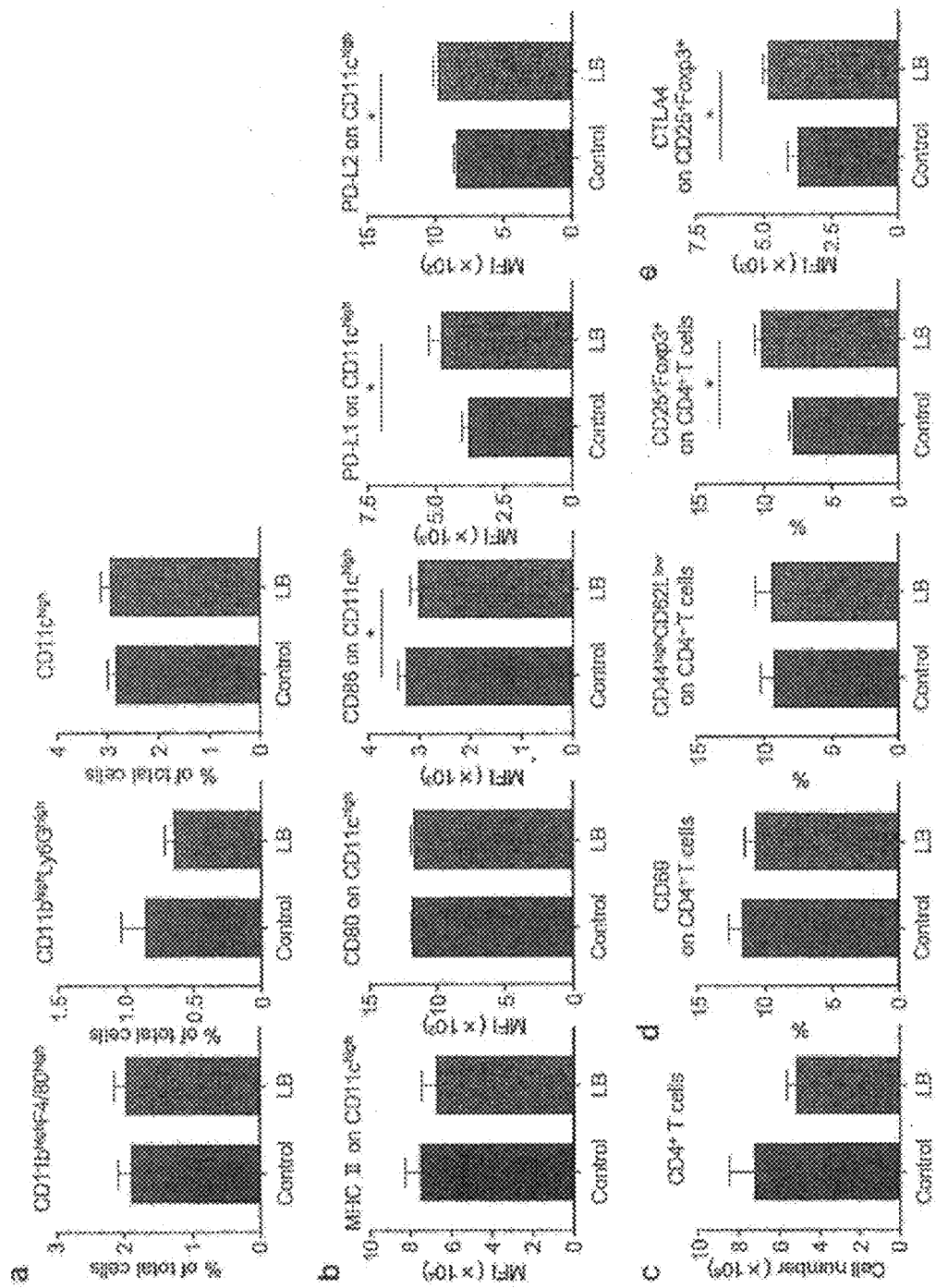

FIG. 9 shows live *Bacteroides* treatment and immune response in the spleen.

Splenocytes were collected from 16-week-old Apoe$^{-/-}$ mice treated with *Bacteroides vulgatus* ATCC 8482$^T$ strain and *Bacteroides dorei* DSM 17855$^T$ strain or a vehicle (control). (a) The percentage of indicated immunocytes in splenocytes (4-5 samples per group). (b) Expression of immunocyte markers in CD11c$^{high}$ antigen presenting cells (4-5 samples per group). (c) The number of CD4$^+$ T cells. (d) Immunocyte markers in the number of CD4$^+$ T cells (5 samples per group). (e) The CTLA4 expression in CD4$^+$ CD25$^+$ Foxp3$^+$ Tregs (5 samples per group). LB: treated with live *Bacteroides vulgatus* ATCC 8482$^T$ strain and *Bacteroides dorei* DSM 17855$^T$ strain; Tregs: regulatory T cells; MFI: mean fluorescence intensity. *P<0.05. To detect a significant difference between two groups, 2-tailed Student's t-test was used. The data shows mean±standard error the mean.

Figure 10:
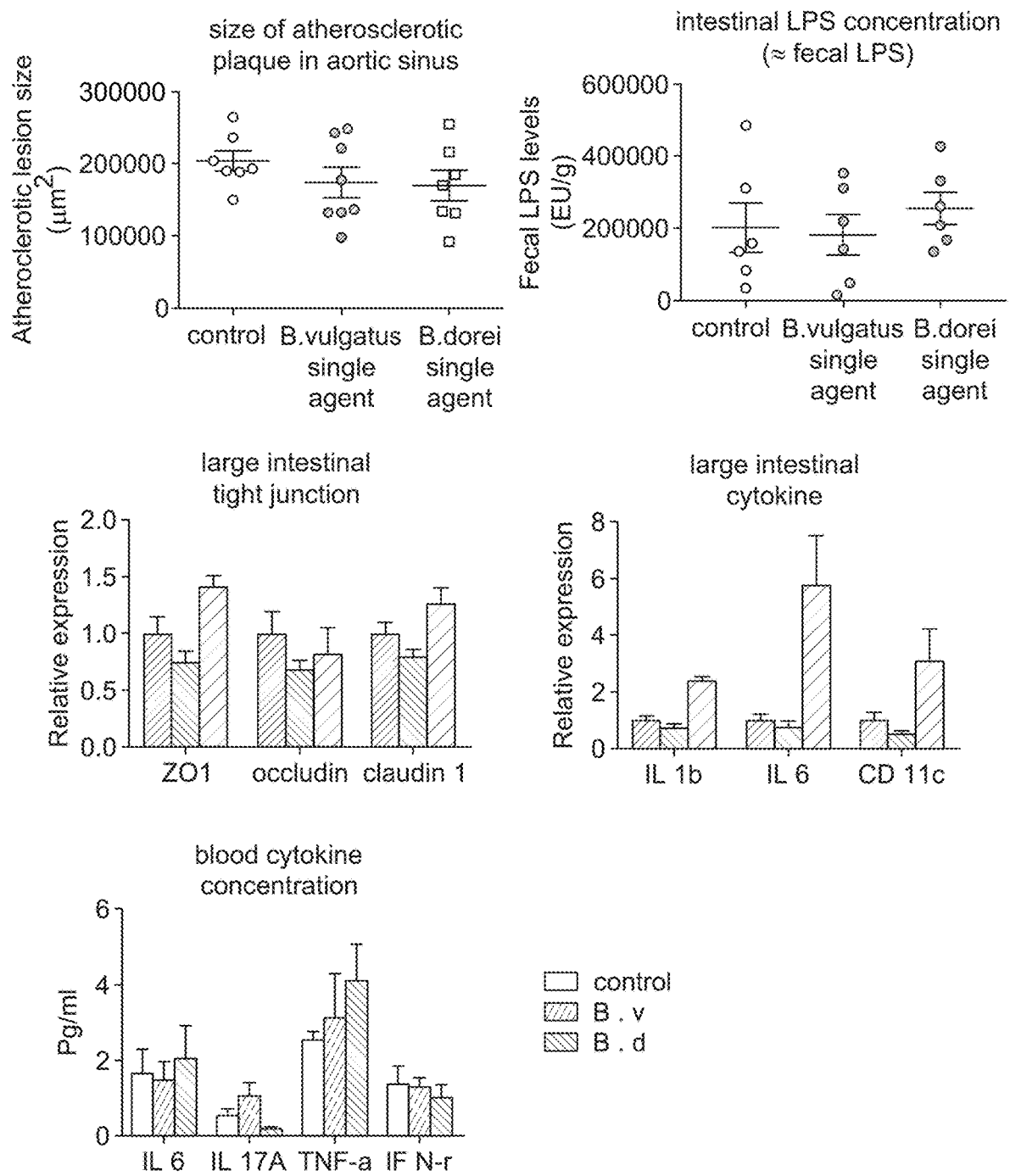

FIG. 10 shows the effect of single administration of live *Bacteroides vulgatus* ATCC 8482$^T$ strain or *Bacteroides dorei* DSM 17855$^T$ strain on ApoE-deficient mice. The control group was orally ingested with vehicle only. The upper left panel shows the size of arteriosclerotic lesions in the aortic sinus, and the upper right panel shows the intestinal (fecal) LPS concentration. The lower left and upper panels show the expression of tight junction related genes in the large intestine, the lower right upper panel shows the expression of cytokine genes in the large intestine, and the lower left and lower panel shows the blood cytokine concentration.

FIG. 11 shows the alignment of 16S rRNA gene of *Bacteroides vulgatus* ATCC 8482$^T$ strain (SEQ ID NO: 1) and 16S rRNA gene of *Bacteroides dorei* JCM 13471$^T$ strain (SEQ ID NO: 3).

Figure 12:
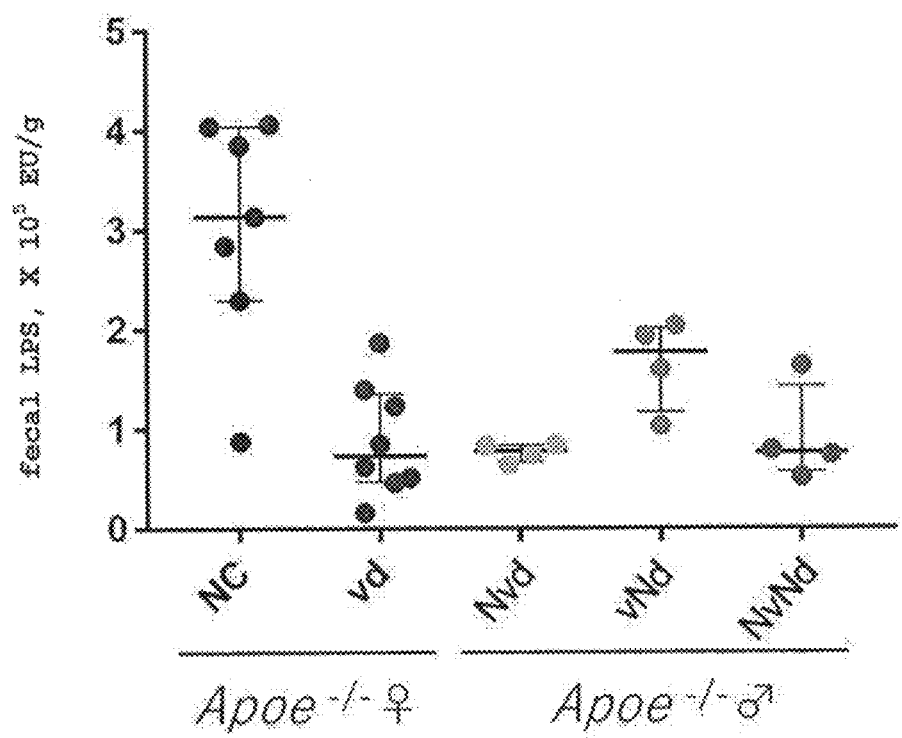

FIG. 12 shows the effect of various combinations of *Bacteroides vulgatus* (ATCC 8482$^T$ strain (v) and NTZ002 strain (Nv)) and *Bacteroides dorei* (DSM 17855$^T$ strain (d) and NTZ001 strain (Nd)) on improving fecal LPS levels in arteriosclerosis mouse model.

Figure 13:
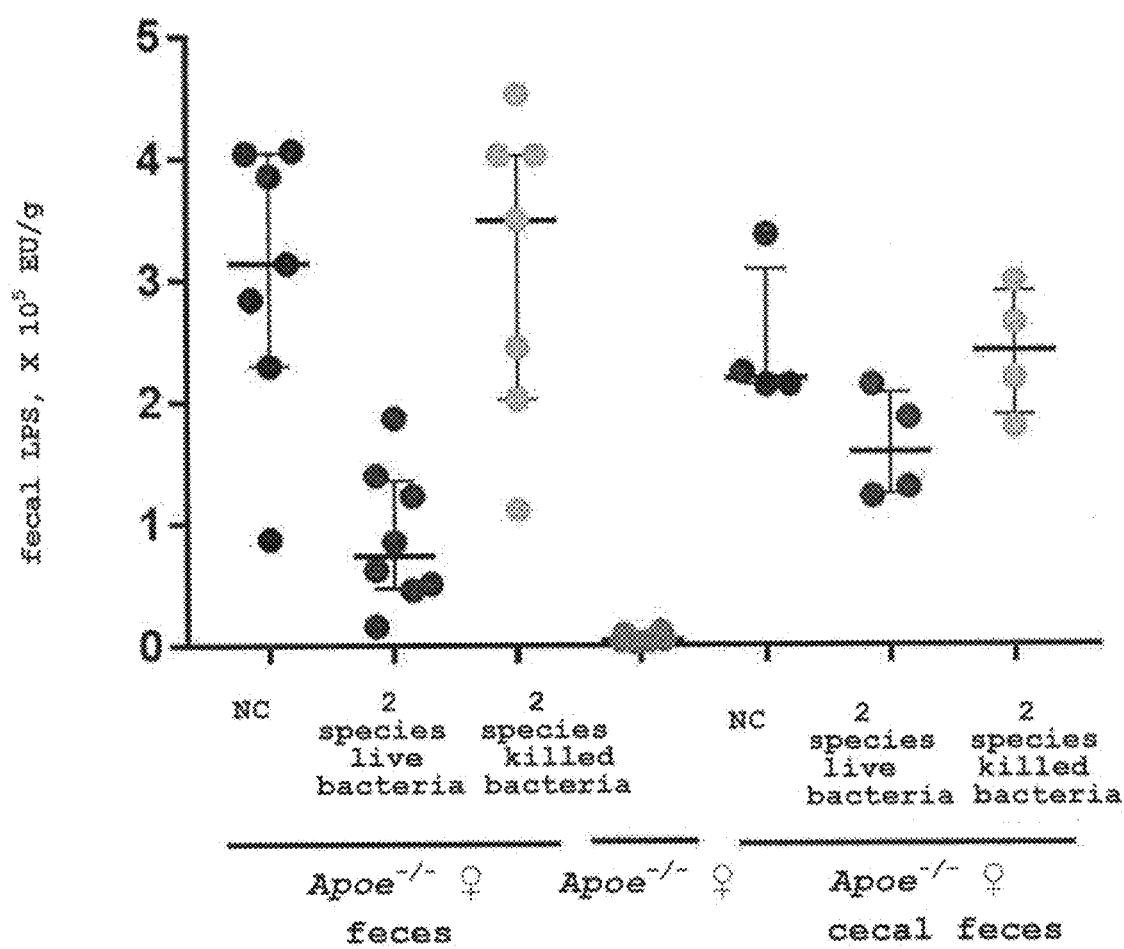

FIG. 13 shows intestinal LPS levels in arteriosclerosis mice, to which live or dead bacteria of *Bacteroides vulgatus* ATCC 8482$^T$ strain and *Bacteroides dorei* DSM 17855$^T$ strain are administered. In the Figure, the left and right sides respectively show the LPS levels in the feces and cecal feces, and the center shows the fecal LPS level of the mice, to which an antibiotic (AVNM) is administered.

Figure 1:
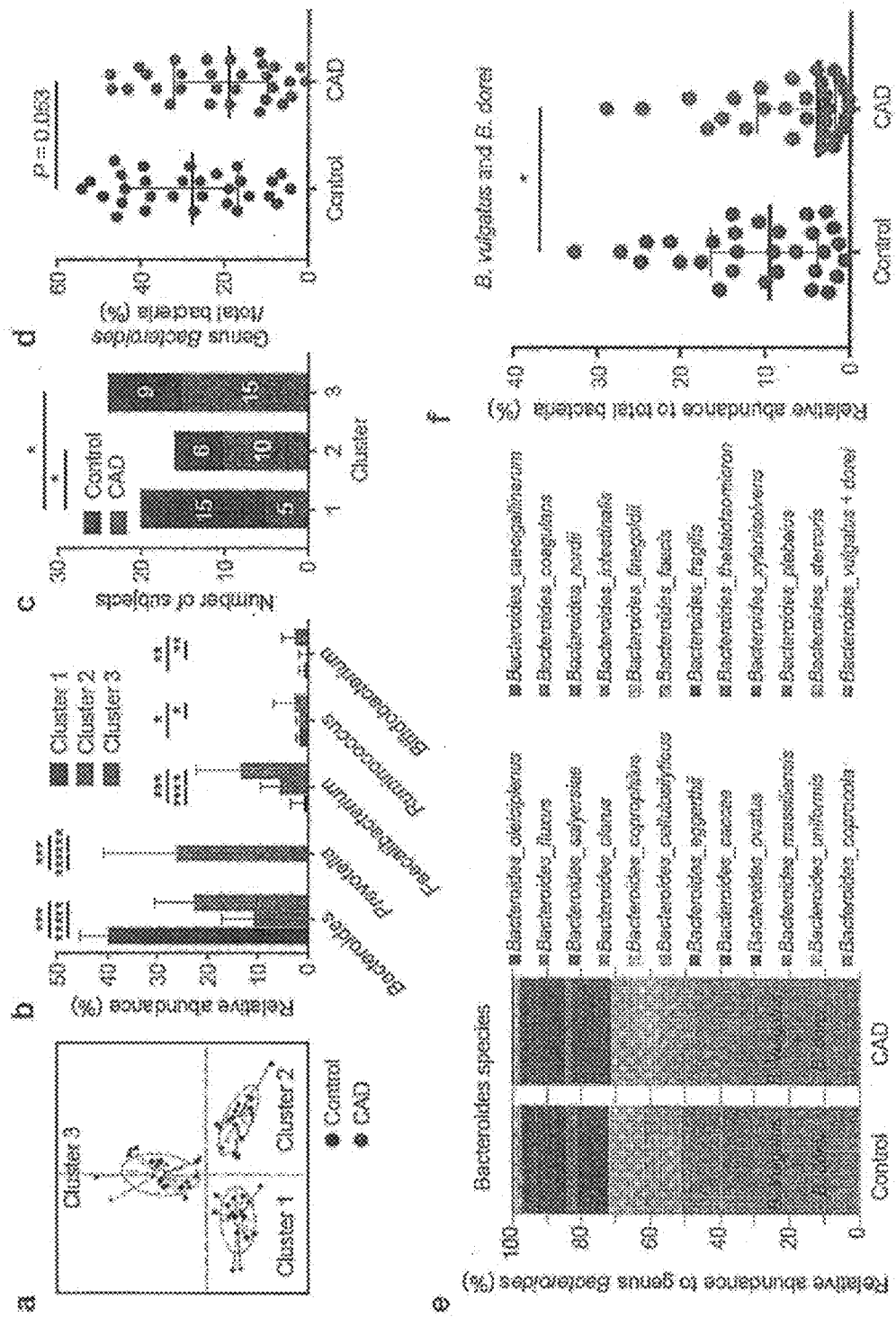
FIG. 1 shows the changes in the intestinal microorganism in CAD patients or non-CAD patients.
Figures 2, 14:
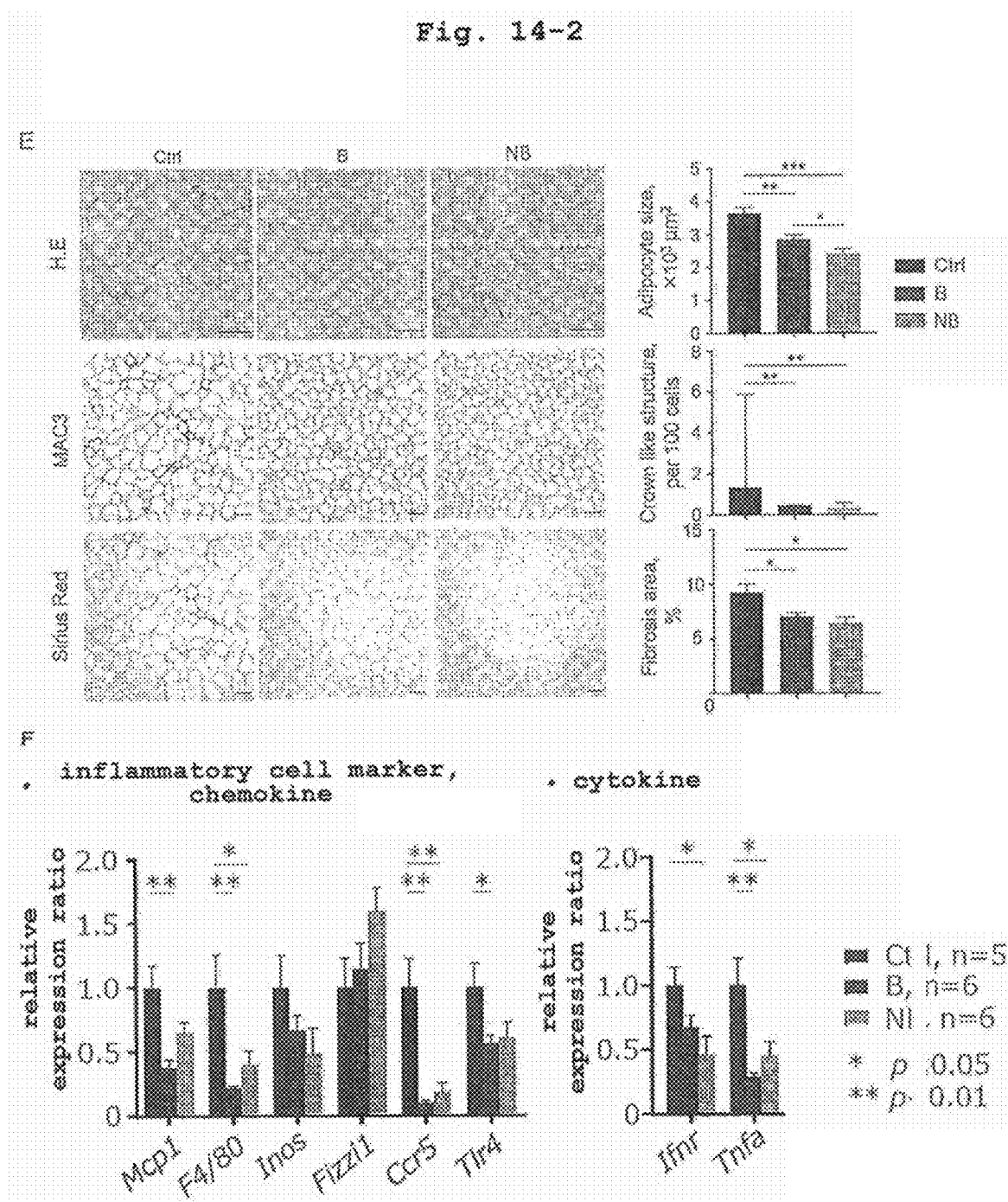

FIG. 14-1 and FIG. 14-2 show improvement of a variety of the symptoms of obesity in the obese mouse model, to which live bacteria of *Bacteroides vulgatus* ATCC 8482$^T$ strain and *Bacteroides dorei* DSM 17855$^T$ strain (B), or *Bacteroides vulgatus* NTZ002 strain and *Bacteroides dorei* NTZ001 strain (NB) are administered. A schematically shows administration protocol of each group. B and C show the changes in the body weight and the changes in the body weight gain of the mice, respectively. D shows the results of the OGTT test (blood glucose level, AUC of blood glucose level, and insulin resistance (HOMA-IR) from left to right).

FIG. 14-2: E shows HE, MAG3 and Sirius Red staining images of epididymal fats specimen (left), adipocyte size, the number of crown-like structures per unit cell, and the ratio of fibrotic regions from the top(right). F shows mRNA expression of inflammatory cell markers or macrophage markers (left) and mRNA expression of cytokines IFNγ and TNFα in the fat around epididymis (right).

Figures 2, 15:
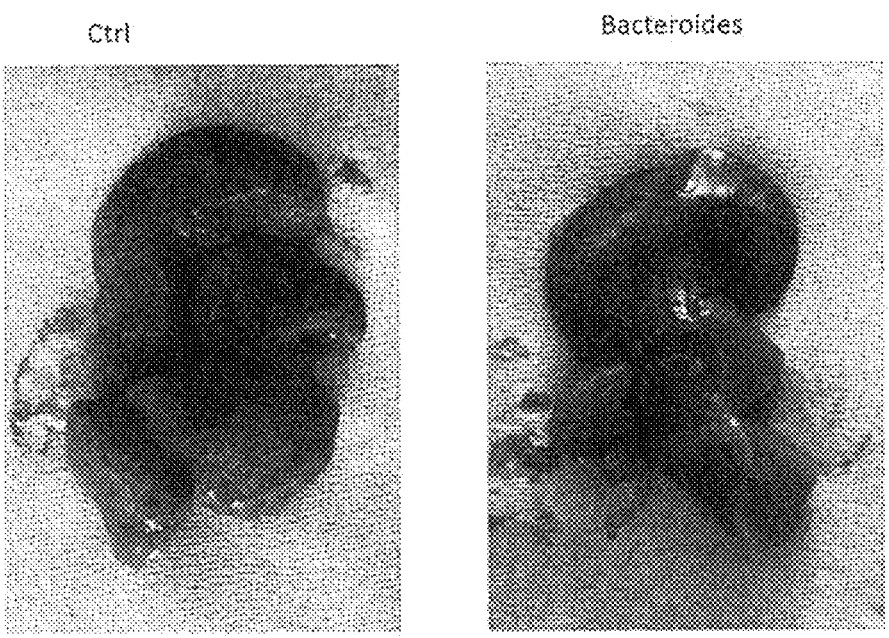

FIG. 15-1 and FIG. 15-2 show improvement of various symptoms of NASH in NASH mouse model, to which live bacteria of *Bacteroides vulgatus* ATCC 8482$^T$ strain and *Bacteroides dorei* DSM 17855$^T$ strain are administered. The upper panel shows HE-stained images of a liver section at 17 weeks of age. The middle panel shows NAFLD activity score (NAS), and the lower panel shows blood AST level and the AST/ALT ratio from left to right.

FIG. 15-2 shows an overview of the excised livers.

DESCRIPTION OF EMBODIMENTS

1. Lipopolysaccharide (LPS)-Regulated Enteric Bacteria

The present invention provides a combination of *Bacteroides vulgatus* and *Bacteroides dorei*, which are the bacteria belonging to the genus *Bacteroides* (hereinafter to be also referred to as "the combination of the present invention"). As used herein, the "combination" means that it may exist as a single composition in which the two are mixed, or may exist in a kit form in which they exist as separate compositions but used in combination for a certain purpose (e.g., medicament, food or food additive, feed, or feed additive). The combination of the present invention can reduce intestinal LPS levels of humans or other animals, strengthen tight junctions in the intestinal barrier to reduce blood LPS levels, and suppress inflammatory responses and immune responses in intestines, in blood vessels, and in organs by co-existing in the intestines thereof (these action effects are sometimes to be comprehensively referred to as "lipopolysaccharide (LPS) controllability" in the present specification).

More specifically, in "the combination of the present invention", (1) a composition comprising a live bacterium of *Bacteroides vulgatus* isolated from nature, and (2) a composition comprising a live bacterium of *Bacteroides dorei* isolated from nature are combined.

The genus *Bacteroides* (*Bacteroides*) is a Gram-negative obligately anaerobic non-sporulating rod-shaped bacterium classified into the eubacteria of Bacteroidetes, Bacteroidia, Bacteroidales, Bacteroidaceae. Currently, 92 species and 5 subspecies are known. The genus *Bacteroides* contains some predominant enteric bacteria in human and is considered to play an important role in maintaining a healthy intestinal ecosystem.

*Bacteroides vulgatus* is one of the bacteria most commonly isolated from the human gastrointestinal tract and is generally considered to be a beneficial commensal bacterium. *Bacteroides dorei* was isolated from human feces and identified in 2006 as a new species closest (about 96% identity) to *Bacteroides vulgatus* by 16S rRNA gene sequencing (Int J Sys Evol Microbiol. 56, 1639-1643, 2006).

In the present specification "isolated from nature" means that it has been artificially manipulated such that the bacterial cell density becomes higher than that in the state originally existing in nature, including not only those completely purified (isolated and purified) but also those containing other contaminants. On the other hand, when a naturally occurring substance such as feces and cecal contents is simply collected, it is not included in those "isolated from nature".

*Bacteroides vulgatus* and *Bacteroides dorei* may be provided by any method as long as they are isolated from nature, which are the active ingredients of the combination of the present invention. For example, those newly isolated from natural separation sources (e.g., feces, contents of gastrointestinal tract, such as cecum and the like, soil, and water) can be used. The preferred separation source is feces of human or other mammals. For example, a fecal sample is suspended in aseptic phosphate buffered saline (PBS), etc., and the obtained suspension is plated on a plate medium suitable for culturing the genus *Bacteroides* bacterium using a platinum loop or the like, and colonies of *Bacteroides vulgatus* and *Bacteroides dorei* can be selected based on bacteriological characteristics (morphological characteristics, biochemical characteristics etc.) of the emerged colony. Typical bacteriological characteristics of the both species are shown as follows.

(1) Macroscopic Characteristics (1-1) White circular colonies raised in a convex shape are formed on a 5% horse blood-added Eggerth Gagnon (EG) agar medium.

(1-2) Microscopic characteristics: rod-shaped bacterium, not motile, does not form spores.

(2) Growth Conditions (2-1) Temperature: Growth at 25-40° C. Optimal temperature 37° C.

(2-2) Obligately anaerobic (3) Physiological and biochemical characteristics (3-1) Gram stainability: negative (3-2) Other biochemical characteristics are shown in Table 1 [In the table, 1 indicates *Bacteroides dorei* JCM13471$^T$ strain, 2 indicates *Bacteroides dorei* JCM13472 strain, and 3 indicates *Bacteroides vulgatus* JCM5826$^T$ strain. Biochemical test was performed using API 20 A and API rapid ID 32 A strips (bioMerieux).] (excerpted from Int J Sys Evol Microbiol. 56, 1639-1643, 2006)

TABLE 1

| Test | 1 | 2 | 3 |
|---|---|---|---|
| API 20 A | | | |
| Urease | − | − | − |
| D-Glucose acidification | + | + | + |
| D-Mannitol acidification | − | − | − |
| D-Lactose acidification | + | + | + |
| D-Maltose acidification | + | + | + |
| Gelatin hydrolysis | − | − | − |
| Glycerol acidification | − | − | − |
| D-Mannose acidification | + | + | + |
| D-Melezitose acidification | − | − | − |
| D-Raffinose acidification | + | + | + |
| D-Sorbitol acidification | − | − | − |
| API rapid ID 32 A | | | |
| D-Arginine dihydrolase | − | − | − |
| α-Galactosidase | + | + | + |
| β-Galactosidase | + | + | + |
| 6-Phospho-β-galactosidase | + | + | + |
| α-Glucosidase | + | + | + |
| β-Glucosidase | + | + | − |
| α-Arabinosidase | + | + | + |
| β-Glucoronidase | + | + | + |
| N-Acetyl-β-glucosoaminidase | + | + | + |
| Glutamic acid decarboxylase | + | + | + |
| Reduction of nitrates | − | − | − |
| Alkaline phosphatase | + | + | + |
| Arginine arylamidase | + | + | + |
| Proline arylamidase | − | − | − |
| Leucyl glycine arylamidase | + | + | + |
| Phenylalanine arylamidase | + | + | − |
| Leucine arylamidase | + | + | − |
| Pyroglutemic acid arylamidase | − | − | − |
| Tyrosine arylamidase | + | + | − |
| Alanine arylamidase | + | + | + |
| Glycine arylamidase | + | + | + |
| Histidine arylamidase | + | + | − |
| Glutamyl glutamic acid arylamidase | + | + | + |
| Serine arylamidase | + | + | − |

Whether a bacterium isolated from the separation source is the strain belonging to *Bacteroides vulgatus* or *Bacteroides dorei*, can be determined by, for example, performing the PCR amplification of all or a part of the 16S rRNA gene while using the genomic DNA extracted from the strain as a template, determining the nucleotide sequence of the amplified fragments, and performing phylogenetic analysis while comparing with the known sequence data of *Bacteroides vulgatus* and *Bacteroides dorei*. The phylogenetic analysis and the preparation method of the phylogenetic tree can be performed, for example, according to the following procedures.

First, the genomic DNA serving as a template is extracted from a bacterium. Methods for extracting DNA from bacteria are known and any method may be used. Generally, a method of treating cells with a cell wall-degrading enzyme, such as lysozyme or the like, a method of physically destroying with glass beads, a treating method of repeating freeze-thawing, or the like is used. In addition, commercially available reagents for DNA extraction can also be used. Genomic DNA does not necessarily require the extraction in an intact state. Thus, the method, that has a low possibility of sample contamination, is easy to operate, and can be performed quickly, can be selected as appropriate.

Then, target DNA encoding 16S rRNA is amplified by polymerase linkage reaction (PCR). The sequences of the primers to be used in PCR can be appropriately designed so that at least the target DNA encoding 16S rRNA of the whole known bacteria belonging to *Bacteroides vulgatus* and/or *Bacteroides dorei*, will be amplified. Generally, primers consisting of sequences that are conserved across species are used (universal primers; for example, the set of 27F and 357R primers, which amplifies approximately 350 bases of V1-V2 region, the set of 342F and 806R primers, which amplifies approximately 460 bases of V3-V4 region and is used in the below-mentioned Example, etc.). The conditions of PCR are not particularly limited, and can be appropriately selected within the range generally used. The reaction can be performed using commercially available PCR reagents and according to the attached instruction.

The DNA fragment amplified by PCR is purified using spin columns or the like as needed, and then the base sequence thereof is determined. The base sequence can be determined by a conventional method.

The determined base sequence is subjected to homology search with a known bacterial 16S ribosome DNA sequence by using an appropriate gene sequence database and homology search program, whereby a known sequence showing the highest homology can be extracted. For example, BLAST and FASTA can be utilized through the Japan DNA Data Bank (DDBJ) web page. When blastn or fasta is selected as a program, the determined base sequence is used as a query, 16S rRNA (Prokaryotes) is selected as a target database, and a search is performed, a known sequence showing high homology is extracted and output. Any other gene sequence databases (e.g., RDP (http://rdp.cme.msu.edu), Silva (http://www.arb-silva.de) etc.) can also be utilized as long as they contain the data set of the base sequence of 16S rRNA gene of bacteria. In addition, a homology search program known per se which is other than the above-mentioned programs can also be used.

In general, for bacteria, the identity of not less than 95% with 16S rRNA gene sequence is required for identification at the genus level, and not less than 98% is required for identification at the species level (Science 2005, 307, 1915-1920). Therefore, when the sequence of 16S rRNA gene of the isolated bacterium has the identity of not less than 98% with a known sequence of the bacterium belonging to *Bacteroides vulgatus* or *Bacteroides dorei* as a result of homology search, the bacterium can be identified as a bacterium belonging to either of these *Bacteroides* species.

Examples of the known 16S rRNA gene sequence serving as a criterion for determination in the case of *Bacteroides vulgatus* include, but are not limited to, the sequence (SEQ ID NO: 1) derived from *Bacteroides vulgatus* ATCC 8482$^T$ strain and registered in GenBank under accession No. NR_074515, the sequence (SEQ ID NO: 2) derived from *Bacteroides vulgatus* JCM5826$^T$ strain and registered under accession No. NR_112946 and the like. Examples of the known 16S rRNA gene sequence of *Bacteroides dorei* include, but are not limited to, the sequence (SEQ ID NO: 3) derived from *Bacteroides dorei* JCM13471$^T$ strain and registered in GenBank under accession No. AB242142, a sequence (SEQ ID NO: 4) derived from *Bacteroides dorei* JCM13472 strain and registered under accession No. AB242143 and the like.

Therefore, when the nucleotide sequence of the aforementioned PCR amplification fragment has the identity of not less than 98% with the nucleotide sequence shown in SEQ ID NO: 1 or 2, the isolated bacterium can be identified as one belonging to *Bacteroides vulgatus*. When the nucleotide sequence of the aforementioned PCR amplification fragment has the identity of not less than 98% with the nucleotide sequence shown in SEQ ID NO: 3 or 4, the isolated bacterium can be identified as one belonging to *Bacteroides dorei*.

It is also possible to assume the molecular evolutionary tree pursuant to the base sequence of the amplified DNA and to specify the taxonomic position of the isolated bacterium. Molecular evolutionary tree analysis softwares are also available on the Internet etc. (CLUSTAL W etc.). As a result of the tree analysis, when the isolated bacterium is located in the same cluster as the one belonging to *Bacteroides vulgatus* or *Bacteroides dorei*, the bacterium can be identified as the one belonging to either *Bacteroides* species.

Alternatively, *Bacteroides vulgatus* and *Bacteroides dorei* used for the combination of the present invention may be the strains that have already been isolated and are commercially available, or that have been preserved and deposited in a depository and can be distributed. Examples of these strains include, but are not limited to, ATCC 8482$^T$ strain, DSM 1447$^T$ strain, JCM 5826$^T$ strain, NERC 14291$^T$ strain, NCTC 11154$^T$ strain, NTZ002strain, and the like for *Bacteroides vulgatus*, and DSM 17855$^T$ strain, JCM 13471$^T$ strain, JCM 13472 strain, NTZ001 strain, and the like for *Bacteroides dorei*. NTZ002 strain and NTZ001 strain were accorded deposit numbers of NITE BP-02863 and NITE BP-02862, respectively, as of Jan. 15, 2019 and internationally deposited at independent administrative institution National Institute of Technology and Evaluation NITE Patented Microorganism Depository (room 122, 2-5-8 Kazusakamatari, Kisarazu-shi, Chiba 292-0818, Japan).

*Bacteroides vulgatus* and *Bacteroides dorei* used in the combination of the present invention may be a combination of any strains as long as it can reduce intestinal LPS levels, strengthen tight junctions in the intestinal barrier to reduce blood LPS levels, and suppress inflammatory responses and immune responses in intestines, in blood vessels, and in organs of humans and other animals by co-existing in the intestines (namely, it can have LPS controllability). A preferable embodiment is, though not limited to, the combinations of *Bacteroides vulgatus* ATCC 8482$^T$ strain or NTZ002 strain, and *Bacteroides dorei* DSM 17855$^T$ strain or NTZ001 strain.

*Bacteroides vulgatus* or *Bacteroides dorei* used in the combination of the present invention may be not only an isolated strain (wild strain) from a natural separation source obtained by any of the above-mentioned means but also a mutant obtained by subjecting same to a mutagenic treatment, as long as LPS controllability is exhibited when one is combined with the other bacteria to be combined, *Bacteroides dorei* or *Bacteroides vulgatus*. Examples of the mutagenic treatment include, but are not limited to, exposure to chemical substances such as nitroso compounds (e.g., nitrosamine, nitrosoguanidine), alkylating agents (e.g., ethyl methanesulfonate (EMS)) and the like, UV or irradiation, radiation irradiation, and the like. As to whether the obtained mutant strain combined with the bacteria to be combined shows LPS controllability when, for example, the mutant strain and bacteria to be combined are administered to a disease animal model (e.g., ApoE-deficient arteriosclerosis mouse model, obese mouse model, and NASH mouse model etc.), and improvement of symptoms and improvement of various parameters (e.g., blood or intestinal LPS level, blood cytokine level, intestine barrier function, body weight, organ weight, histopathological examination, etc.) are found, the mutant strain can be determined to have LPS controllability. Alternatively, when immunocytes, such as macrophage and the like, are stimulated with the fecal supernatant of the animal model, and the mutant strain and the bacteria to be combine are added, and then a suppressive effect on the proliferation of the cells or the production of inflammatory cytokine is shown, the mutant strain can be determined to have LPS controllability.

The thus-obtained *Bacteroides vulgatus* and *Bacteroides dorei* can be maintained and amplified by culturing under culture conditions known per se.

As the medium, ATCC Medium 2107 (peptone 10 g, beef extract 10 g, yeast extract 3 g, dextrose 5 g, NaCl 5 g, soluble starch 1 g, L-cysteine hydrochloride 0.5 g, sodium acetate 3 g, 0.025% Resazurin 4 mL, and distilled water 1 L), ATCC Medium 260 (tryptone 15 g, Soytone 5 g, NaCl 5 g, defibrinated sheep blood 50 mL, and distilled water 950 mL), 5% horse blood-added EG medium, and the like can be used. These media can also be used as liquid media or solid media by, for example, adding 1.5% agar.

Since *Bacteroides vulgatus* and *Bacteroides dorei* are obligately anaerobic bacteria, their cultivation must be proceeded under anaerobic conditions (that the oxygen concentration is not more than 1 ppm). For example, they can be cultured in an anaerobic gas chamber under a mixed gas atmosphere of 10% $CO_2$, 10% $H_2$ and 80% $N_2$. The culture temperature is 25-40° C., preferably about 37° C. The culture period is not particularly limited, which includes 12-72 hr, preferably 24-48 hr.

*Bacteroides vulgatus* and *Bacteroides dorei* can also be mixed and cultured in the same medium as long as they do not adversely affect the growth and biological activity of each other. In addition, *Bacteroides vulgatus* and *Bacteroides dorei* contained in the combination of the present invention may each be a single strain or a mixture of two or more strains.

The thus-obtained culture of *Bacteroides vulgatus* and *Bacteroides dorei* can be freezed and stored until use, for example, like a glycerol stock by a method known per se at not more than −80° C., or can be freeze-dried by a method known per se and stored at 2-8° C.

2. The Combination of the Present Invention

*Bacteroides vulgatus* and *Bacteroides dorei* as the above-mentioned culture (bacterial cell) itself, or in the state of a "processed bacterial cell product" such as a wet bacterial cell material collected from the culture by a method known per se, for example, methods, such as centrifugation, filtration, magnetic separation, and the like, a washed material thereof (can be washed with sterilized water, medium, PBS, and the like), a freeze-dry powder thereof, or the like, as long as it is in a living state (live bacterium), can be blended in a composition containing them. In the present specification, unless otherwise specified, the "bacterial cell" or "processed bacterial cell product" is hereinafter used to mean that it does not include those in a "non-living" state such as dead bacteria, disrupted bacterial cells, bacterial cell extract, bacterial cell components, and the like.

The bacterial cell or processed bacterial cell product of *Bacteroides vulgatus*, and bacterial cell or processed bacterial cell product of *Bacteroides dorei* can be formulated alone or with a pharmaceutically acceptable additive or an additive acceptable for food or feed processing. Alternatively, the bacterial cell or processed bacterial cell product can be blended in a pharmaceutical composition, food, or feed as a pharmaceutical additive or food pr feed additive. In the combination of the present invention, the bacterial cell or processed bacterial cell product of *Bacteroides vulgatus*, and bacterial cell or processed bacterial cell product of *Bacteroides dorei* may be formulated as separate compositions and used as a kit formulation. However, they are preferably blended in the same composition and used as a single formulation.

When the bacterial cell or processed bacterial cell product of *Bacteroides vulgatus*, and bacterial cell or processed bacterial cell product of *Bacteroides dorei* are provided as separate compositions, the compositions may be inoculated simultaneously or at different times by the same route or different routes.

When the combination of the present invention is provided as a pharmaceutical product or pharmaceutical additive, the pharmaceutical product or pharmaceutical product containing the additive may be formulated as, for example, powder, granule, pill, soft capsule, hard capsule, tablet, chewable tablet, quick-disintegrating tablet, syrup, liquid, suspension, suppository, injection, or the like.

Examples of the composition for oral administration include solid or liquid dosage form, specifically tablet (including sugar-coated tablet, film-coated tablet), pill, granule, powder, capsule (including soft capsule), syrup, emulsion, suspension, and the like. Such compositions are produced by a known method, and may contain additives generally used in the pharmaceutical field, such as excipient, binder, disintegrant, lubricant, and the like. Examples of the excipient include animal and plant oils, such as soybean oil, safflower oil, olive oil, germ oil, sunflower oil, beef tallow, sardine oil, and the like, polyvalent alcohols, such as polyethylene glycol, propylene glycol, glycerol, sorbitol, and the like, surfactants, such as sorbitan fatty acid ester, sucrose fatty acid ester, glycerin fatty acid ester, polyglycerol fatty acid ester, and the like, purified water, lactose, starch, crystalline cellulose, D-mannitol, lecithin, gum arabic, sorbitol solution, carbohydrate solution, and the like. Examples of the binder include hydroxypropylmethylcellulose, hydroxypropylcellulose, gelatin, pregelatinized starch, polyvinylpyrrolidone, polyvinylalcohol, and the like. Examples of the disintegrant include carmellose calcium, carmellose sodium, croscarmellose sodium, crospovidone, low-substituted hydroxypropylcellulose, cornstarch, and the like. Examples of the lubricant include talc, hydrogenated vegetable oil, waxes, light anhydrous silicic acid and the like derived from naturally occurring substance and derivatives thereof, stearic acid, magnesium stearate, calcium stearate, aluminum stearate, and the like.

The above-mentioned composition can further contain a sweetener, a colorant, a pH adjuster, a flavor, various amino acids, and the like. Also, tablet and granule may be coated by a well-known method. A liquid preparation may be dissolved or suspended in water or other suitable medium when it is taken.

As the composition for parenteral administration, injection, suppository, and the like are used. A preparation method of injection includes, for example, suspending or emulsifying bacterial cells of *Bacteroides vulgatus* or *Bacteroides dorei* or a processed bacterial cell product thereof of the present invention in an aseptic aqueous solution or oily solution generally used for injection. As an aqueous solution for injection, saline, isotonic solution containing glucose or other auxiliary agents, and the like are used. As an oily solution, for example, sesame oil, soybean oil, and the like are used. A suppository for rectal administration can be prepared by mixing bacterial cells of *Bacteroides vulgatus* or *Bacteroides dorei* or a processed bacterial cell product thereof with a general base for suppository.

When it is further provided as a pharmaceutical product or pharmaceutical additive, the combination of the present invention may be used in combination with other medicaments, for example, antiinflammatory drug, antiarteriosclerosis drug, antidiabetic drug, and the like according to the target disease. The combination of the present invention and a companion drug may be formulated as a single composition (combination agent) or may be provided as separate compositions. When provided as separate compositions, the combination of the present invention and the concomitant drug can be administered to a subject by the same route or different routes simultaneously or at different times.

When the combination of the present invention is provided as a food (or feed) or food additive (or feed additive), the food (or feed) or food (or feed) containing the additive is not particularly limited as long as it permits oral ingestion, such as solution, suspension, powder, solid formed articles, and the like. Specific examples include supplements (powder, granule, soft capsule, hard capsule, tablet, chewable tablet, quick-disintegrating tablet, syrup, liquid etc.), drinks (carbonic acid drinks, lactic acid drinks, sport drinks, fruit juice drinks, vegetable drinks, soymilk drink, coffee drinks, tea drinks, powder drinks, concentrated drinks, nutrition drinks, alcohol drinks etc.), dairy products (yogurt, butter, cheese, ice cream etc.), confectionery (gummy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, cream, margarine etc.), wheat powder products (bread, pasta, noodle, cake mix, bread crumb etc.), seasoning (sauce, tomato processing seasoning, flavor seasoning, cooking mixture, soup etc.), and processed meat products (meat ham, sausage etc.).

The above-mentioned foods (or feed) can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, Agaricus, and the like.

The number of viable counts of *Bacteroides vulgatus* and *Bacteroides dorei* contained in the combination of the present invention is, for example, $10^4$-$10^{12}$ colony formation unit (cfu), preferably $10^6$-$10^{10}$ cfu, as an amount of daily ingestion.

The combination of the present invention can be further blended with other beneficial bacteria cells or their processed bacterial products. Examples of such other microorganisms include, but are not limited to, lactic acid bacteria belonging to the genus *Lactobacillus*, genus *Streptococcus*, genus *Leuconostoc*, genus *Pediococcus*, genus *Lactococcus*, genus *Enterococcus*, genus *Bifidobacterium*, and the like, yeast, genus *Bacillus, Clostridium butyricum, Aspergillus oryzae*, and the like. These companions can also be blended with the combination of the present invention not only in the form of live bacteria but also in that of dead bacteria or bacterial cell homogenates, bacterial cell extracts, bacterial cell components, and the like as long as the effectiveness is recognized.

The amount of the combined microorganism is, for example, $10^4$-$10^{12}$ colony forming units (cfu), preferably $10^6$ to $10^{10}$ cfu, as an amount of daily ingestion.

3. The Use of the Combination of the Present Invention

As mentioned above, *Bacteroides vulgatus* and *Bacteroides dorei* can reduce intestinal LPS levels by co-existing in the intestines thereof, strengthen tight junctions in the intestinal barrier to reduce blood LPS levels, and suppress inflammatory responses and immune responses in the intestines, in blood vessels, and in organs (namely, having LPS controllability). Thus, enrichment of the both bacterial species in the intestinal microflora can prevent and/or improve diseases associated with elevated blood or intestinal LPS levels. Therefore, the combination of the present invention is useful as a pharmaceutical product or pharmaceutical additive, or functional food (or feed) or food (or feed) additives for preventing and/or improving these diseases.

Examples of the disease associated with elevated blood or intestinal LPS levels include circulatory diseases, such as atrial fibrillation, cardiac failure, ischemic cardiac diseases, myocardial infarction, angina pectoris, hypertension, arteriosclerosis, aneurysm of aorta, aortic dissection, arteriosclerosis obliterans, aortic stenosis, and the like, inflammatory diseases such as, for example, hepatitis, non-alcoholic steatohepatitis, fatty liver, liver cancer due to progression of hepatitis, intestinal inflammation, irritable bowel syndrome, gastritis, collagen disease, chronic rheumatoid arthritis, chronic nephritis, IgA nephropathy, bronchial asthma, interstitial pneumonia, drug-induced lung disorder, pulmonary infiltration with eosinophilia syndrome, atypical mycobacteriosis, allergic rhinitis, atopic dermatitis, sepsis, and the like, metabolic diseases, such as diabetes, obesity, metabolic syndrome, lifestyle-related disease, dyslipidemia, osteoporosis, and the like, and the like.

The combination of the present invention can be used for humans or other mammals (e.g., dog, cat, mouse, rat, hamster, guinea pig, rabbit, swine, bovine, goat, horse, sheep, monkey etc.) by giving a daily amount of the above-mentioned oral ingestion once a day or in several divided portions per day. Alternatively, it may be administered rectally.

When the combination of the present invention is provided as a food, the food can be sold with the indication that it is used for prevention and/or improvement of diseases associated with elevated blood or intestinal LPS levels. Here, "the indication" means all the acts, which is for informing the consumer of the above-mentioned use, and any indication that can recall or analogize the above-mentioned use falls under "the indication" in the present invention, regardless of the purpose of indication, the content of indication, and object, medium, etc. to be indicated. It is preferable, however, to display using the expressions that allow the consumer to directly recognize the above-mentioned use. The specific examples include the act of describing the above-mentioned use on a product or a product package relating to the food of the present invention, the act of assigning or handing over the product or the product package describing the above-mentioned use or that of exhibiting for assigning or hanging over or importing for assignment or hanging over same, and the act of describing the above-mentioned use on advertisements, price lists, or transaction documents relating to the products to exhibit or to distribute same, or that of providing information containing these contents and carrying the above-mentioned use by an electromagnetic method (Internet etc.).

On the other hand, the indication is preferably one approved by the administration and the like (for example, the indication approved based on each system established by the administration and performed in a manner based on such approval). Particularly, the indication on package, container, catalog, pamphlet, advertising material at sales sites such as POP, and other documents, and the like is preferable.

In addition, for example, indications of health food, functional food, enteral nutritional food, food for special dietary uses, food with nutrient function claims, and quasi-drugs can be exemplified. Other examples include indications approved by the Ministry of Health, Labor and Welfare, such as foods for specified health uses and indications approved by a similar system. The latter examples include indications for a food for specified health use, a food for specified health care with conditions, the indication that the structure and function of the body are affected, a disease risk reduction indication, and the like. To be more specific, the indication as a food for specified health use (in particular, the indication of health use) stipulated in the Ordinance for Enforcement of Health Promotion Act (Ordinance of the Ministry of Health, Labour and Welfare of Japan, No. 86 of Apr. 30, 2003), and an indication similar thereto can be recited.

4. The Test Method of the Present Invention and Reagent Therefor

The present invention also provides a method for testing the risk of developing a disease related to an elevated blood or intestinal LPS levels (hereinafter to be also referred to as "LPS associated disease"), the method including measuring the abundance of *Bacteroides vulgatus* and *Bacteroides dorei* in the intestinal microflora of a test subject (hereinafter to be also referred to as "the test method of the present invention") and a reagent therefor (hereinafter to be also referred to as "the test drug of the present invention"). As shown in the below-mentioned Example, the abundance of *Bacteroides vulgatus* and *Bacteroides dorei* significantly decreases in the intestinal microflora of patients with coronary heart disease (CAD). Also, when the both species are orally ingested to arteriosclerosis mouse model, they can improve the symptoms of arteriosclerosis, reduce intestinal LPS levels, strengthen tight junctions in the intestinal barrier to reduce blood LPS levels, and suppress inflammatory responses and immune responses in the intestines and blood vessels (namely, having LPS controllability). Moreover, when the both species are orally ingested to obese mouse model, they can improve the symptoms of obesity and suppress inflammatory responses and immune responses in the organs. Furthermore, when the both species are orally ingested to alcoholic steatohepatitis model mice, they can improve the symptoms of non-alcoholic steatohepatitis and suppress inflammatory responses and immune responses in the organs. Therefore, by measuring the abundance of *Bacteroides vulgartus* and *Bacteroides dorei* in the intestinal microflora of the test subject, and comparing same with the normal value, it is possible to determine whether the subject has an LPS-related disease or a high risk of developing the disease in the future. In the present specification, the "test for risk of onset" is used to mean not only a test for predicting the probability of onset in the future but also a test for diagnosing whether the disease has already been developed. In the present specification, the term "detection" is used to include not only determining the presence or the absence of the bacterium of interest but also quantitatively measuring the abundance thereof, unless such interpretation is clearly incorrect.

The test subject in the test method of the present invention is not particularly limited. For example, those who are suspected to have LPS-related diseases such as circulatory disease, inflammatory disease, and metabolic disease in clinical findings, and the patients who have already been found to have these diseases may be included. Once a decrease in the abundance of *Bacteroides vulgatus* and *Bacteroides dorei* in the intestinal microflora is known, enrichment of the species in the intestinal microflora can be one of the therapeutic targets for the patient. As the sample derived from the subject for the test, feces are preferred from the ease of collection; note that the sample is not particularly limited as long as it can reflect the intestinal microflora of the subject. For example, it may be intestinal contents (e.g., cecal contents) or the like.

The search for *Bacteroides vulgatus* and *Bacteroides dorei* can be executed by, for example, detecting the 16S rRNA gene that the species has: specifically, 16S rRNA gene containing a nucleotide sequence having the identity of not less than 98% with the nucleotide sequence shown in SEQ ID NO: 1 or 2 in the case of *Bacteroides vulgatus*, or 16S rRNA gene containing a nucleotide sequence having the identity of not less than 98% with the nucleotide sequence shown in SEQ ID NO: 3 or 4 in the case of *Bacteroides dorei*.

For the detection of the 16S rRNA gene of *Bacteroides vulgatus* and *Bacteroides dorei*, firstly, total DNA is recovered from the sample. The methods for isolating/purifying DNA from the fecal sample of the test subjects are known in the pertinent technical field. It can be performed by, for example, extraction with phenol/chloroform, extraction with a commercially available DNA extraction reagent, or purification with a commercially available column kit, etc.

The DNA collected from the samples is dissolved in an appropriate buffer, for example, TE (10 mM Tris-HCl, 1 mM EDTA, pH 8.0) and the like, and subjected to the detection of 16S rRNA gene.

In one embodiment, 16S rRNA gene is detected by PCR using the primers, which is capable of specifically amplifying the 16S rRNA gene of *Bacteroides vulgatus*, i.e., 16S rRNA gene containing a nucleotide sequence having the identity of not less than 98% with the nucleotide sequence shown in SEQ ID NO: 1 or 2, and/or 16S rRNA gene of *Bacteroides dorei*, i.e., 16S rRNA gene containing a nucleotide sequence having the identity of not less than 98% with the nucleotide sequence shown in SEQ ID NO: 3 or 4, and DNA recovered from the sample as a template.

The above-mentioned primers may be any as long as they are designed such that they can specifically PCR-amplify a part or all of the region of the above-mentioned 16S rRNA gene. Here, "specifically" means that the primers PCR-amplifies a part or the whole region of the 16S rRNA gene of *Bacteroides vulgatus* and/or *Bacteroides dorei*, but does not PCR-amplify the 16S rRNA gene other than the species of interest.

The above-mentioned primers are, for example, the one pair of polynucleotides which is a combination of the polynucleotide containing a nucleotide sequence of about 15 to about 50 bases, preferably about 18-about 30 bases, which hybridizes to a continuous partial sequence of a complementary sequence of a nucleotide sequence having an identity of not less than 98% with the nucleotide sequence shown in SEQ ID NO: 1 or 2 (preferably, the nucleotide sequence shown in SEQ ID NO: 1 or 2) and/or a continuous partial sequence of a complementary sequence of a nucleotide sequence having identity of not less than 98% with the nucleotide sequence shown in SEQ ID NO: 3 or 4 (preferably, the nucleotide sequence shown in SEQ ID NO: 3 or 4), and the polynucleotide containing a nucleotide sequence of about 15-about 50 bases, preferably about 18-about 30 bases, which hybridizes to a continuous partial sequence of the above-mentioned nucleotide sequence on the 3'-side from the hybridization site, wherein the nucleic acid amplified thereby has a fragment length of about 50-about 1,000 bases, preferably about 100-about 500 bases.

The primers preferably contain a partial sequence of consecutive 15-50 bases (preferably 18-30 bases), or a partial sequence of a complementary sequence of consecutive 15-50 bases (preferably 18-30 bases) of a nucleotide sequence having the identity of not less than 98% with the nucleotide sequence shown in SEQ ID NO: 1 or 2 (preferably, the nucleotide sequence shown in SEQ ID NO: 1 or 2) and/or a nucleotide sequence having the identity of not less than 98% with the nucleotide sequence shown in SEQ ID NO: 3 or 4 (preferably, the nucleotide sequence shown in SEQ ID NO: 3 or 4).

From the aspects of specificity, the nucleotide sequence shown in SEQ ID NO: 1 or 2 and/or the nucleotide sequence shown in SEQ ID NO: 3 or 4 of at least one of the preferable primer set has a nucleotide sequence located in any of the nine variable regions (V1 to V9), that differ in sequence among the bacterial species contained in the 16S rRNA gene, or a nucleotide sequence complementary to a complementary strand sequence thereof.

In the test method of the present invention, 16S rRNA gene of Bacteroides vulgatus and the 16S rRNA gene of Bacteroides dorei may be detected separately, or both may be detected collectively without making a distinction. As shown in the below-mentioned Comparative Example, oral ingestion of either Bacteroides vulgatus or Bacteroides dorei alone in arteriosclerosis mouse model showed a tendency toward improvement of the symptoms of arteriosclerosis, but a significant difference was not observed, and intestinal LPS levels could not be lowered. Therefore, while it is desirable to separately detect Bacteroides vulgatus and Bacteroides dorei, it is unlikely that the abundance of only one of them will significantly change in the intestinal microflora. Even if both are detected collectively, it does not substantially affect the judgment results.

For example, when the 16S rRNA gene (SEQ ID NO: 1) of Bacteroides vulgatus ATCC 8482$^T$ strain and the 16S rRNA gene (SEQ ID NO: 3) of Bacteroides dorei JCM 13471$^T$ strain are aligned using BLAST (NCBI) under default conditions, the results are as shown in FIG. 11 (Query is SEQ ID NO: 1, Sbjct is SEQ ID NO: 3). The both sequences overlap over 1493 nucleotides (positions 12 to 1497 of SEQ ID NO: 1, positions 1 to 1490 of SEQ ID NO: 3; gap number 10) and show the high homology of about 97% (1449/1493) identity. Therefore, the designed regions of the Bacteroides vulgatus-specific primer and the Bacteroides dorei-specific primer, which are capable of distinguishing and amplifying the 16S rRNA genes of Bacteroides vulgatus and Bacteroides dorei, are limited. For example, positions 181-210 of SEQ ID NO:1 show only about 73% (22/30) identity with the corresponding region of SEQ ID NO:3, and positions 1001-1028 of SEQ ID NO:1 show only about 60% (18/30) identity with the corresponding region of SEQ ID NO: 3. Thus, it is possible to distinguish and amplify the 16S rRNA gene of Bacteroides vulgatus and 16S rRNA gene of Bacteroides dorei by designing either one or both primers in these regions.

On the other hand, when 16S rRNA genes of Bacteroides vulgatus and Bacteroides dorei are collectively amplified, for example, the 16S rRNA genes of both bacterial species can be amplified collectively without amplifying 16S rRNA genes of other enteric bacteria by using the primer set (amplifying positions 136 to 608 of SEQ ID NO: 1 and positions 125 to 599 of SEQ ID NO: 3) described as a Bacteroides vulgatus-specific primer in Tomotari Mitsuoka Ed. "Molecular ecological detection and identification of intestinal microflora" p 109-121 (2000) (Bacteroides dorei was unidentified then).

When this primer set is used, the amplified fragment of SEQ ID NO: 1 has one TaqI restriction site (TOGA; positions 288 to 291 of SEQ ID NO: 1), but the amplified fragment of SEQ ID NO: 3 does not have a TaqI restriction site. When the amplified fragment is digested with TaqI and electrophoresed, two bands of 153 bp and 320 bp are detected when only Bacteroides vulgatus is present; when only Bacteroides dorei is present, one band of 475 bp is detected. When the both species are present, the above-mentioned 3 bands are detected. Therefore, Bacteroides vulgatus and Bacteroides dorei can also be detected separately by the primers, which are capable of collectively amplifying the both bacterial species, in combination with RFLP analysis.

The temperature, reaction time, and number of cycles in PCR can be appropriately set according to the amount of template DNA to be used, the kind of primers, and the like. The annealing temperature in PCR can be appropriately set based on the GC content of the primers.

The obtained PCR products are separated by electrophoresis (e.g., agarose gel electrophoresis, polyacrylamide gel electrophoresis, etc.). After electrophoresis, the gel is stained with a staining solution known per se such as ethidium bromide solution and the PCR product is detected using a transilluminator or the like. Then, the presence or absence and the abundance of Bacteroides vulgatus and/or Bacteroides dorei in the sample are determined using the presence or absence or the amount of the specific PCR product as an index.

The PCR used in the test method of the present invention may be quantitative PCR. Quantitative PCR can be performed by a known method, and two analysis methods are known. The first one utilizes the character of the reaction product exponentially increasing up to a certain amount in the PCR reaction and then reaching a plateau, and analyzes the amount of the reaction product during the exponential increase period and calculates the amount of initial template. The second one is a method of monitoring the reaction products in real time to determine the number of PCR cycles (Ct), in which the amount of the reaction product exceeds a certain value (threshold). All analysis methods require performing PCR in varying amounts of DNA of a known concentration, analyzing the reaction product at each cycle number, and determining the range of quantitative PCR cycle number from the kinetics thereof. The abundance of the target gene in an unknown sample is estimated based on the results. The abundance of Bacteroides vulgatus and/or Bacteroides dorei in the sample can be quantified thereby. When even one copy of the gene of interest is estimated to be contained in the test sample, it is determined that the target bacterium is present.

In another embodiment, 16S rRNA gene can be detected by bringing the probe, which is capable of specifically hybridizing the 16S rRNA gene of Bacteroides vulgatus, i.e., 16S rRNA gene containing a nucleotide sequence having the identity of not less than 98% with the nucleotide sequence shown in SEQ ID NO: 1 or 2, and/or 16S rRNA gene of Bacteroides dorei, i.e., 16S rRNA gene containing a nucleotide sequence having the identity of not less than 98% with the nucleotide sequence shown in SEQ ID NO: 3 or 4 in contact with total DNA or total RNA in the sample, and detecting the hybrid. The contact conditions are appropriately set such that the probe hybridizes with 16S rRNA or a gene encoding the same to form a nucleic acid complex. The complex is then detected as an indication of the presence of Bacteroides vulgates and/or Bacteroides dorei.

The above-mentioned probe is the polynucleotide, that hybridizes, under stringent conditions, to a continuous nucleotide sequence of about 15 bases or more, preferably about 18-about 500 bases, more preferably about 18-about 200 bases, further preferably about 18-about 50 bases, contained in a nucleotide sequence having the identity of not less than 98% with the nucleotide sequence shown in SEQ ID NO: 1 or 2 (preferably, the nucleotide sequence shown in SEQ ID NO: 1 or 2) and/or a nucleotide sequence having the identity of not less than 98% with the nucleotide sequence shown in SEQ ID NO: 3 or 4 (preferably, the nucleotide sequence shown in SEQ ID NO: 3 or 4), or a complementary sequence of the continuous nucleotide sequence.

The hybridization can be performed according to a method known per se or a method analogous thereto, for example, the method described in Molecular Cloning, 2nd edition (J. Sambrook et al., Cold Spring Harbor Lab. Press, 1989) and the like. Examples of stringent conditions include, for example, a hybridization reaction in 6×SSC (sodium chloride/sodium citrate) at 45° C., and then washing once or more in 0.2×SSC/0.1% SDS at 65° C. and the like. Those skilled in the art can easily adjust to the desired stringency by appropriately changing the salt concentration of the hybridization solution, the temperature of the hybridization reaction, the probe concentration, the length of the probe, the number of mismatches, the time of hybridization reaction, the salt concentration of the washing solution, the temperature of washing, and the like.

Preferably, the probe is a nucleic acid containing a continuous nucleotide sequence of about 15 bases or more, preferably about 18-about 500 bases, more preferably about 18-about 200 bases, further preferably about 18-about 50 bases, contained in a nucleotide sequence having the identity of not less than 98% with the nucleotide sequence shown in SEQ ID NO: 1 or 2 (preferably, the nucleotide sequence shown in SEQ ID NO: 1 or 2) and/or a nucleotide sequence having the identity of not less than 98% with the nucleotide sequence shown in SEQ ID NO: 3 or 4 (preferably, the nucleotide sequence shown in SEQ ID NO: 3 or 4), or a complementary sequence of the continuous nucleotide sequence.

From the aspects of specificity, a preferable probe is, for example, the nucleic acid, that hybridizes, under stringent conditions, to a nucleotide sequence located in any of the nine variable regions (V1 to V9), that differ in sequence among the bacterial species contained in the 16S rRNA gene in the nucleotide sequence shown in SEQ ID NO: 1 or 2, or the nucleotide sequence shown in SEQ ID NO: 3 or 4, or a complementary sequence thereof. Specifically, the regions exemplified as the above-mentioned designed region of the primer, which are recognized to have the relatively low homology, in the alignment of SEQ ID NO: 1 and SEQ ID NO: 3 shown in FIG. 11, can be similarly mentioned. Alternatively, a nucleic acid containing a region exemplified as the primer, which is capable of specifically and collectively amplifying the 16S rRNA gene of *Bacteroides vulgatus* and the 16S rRNA gene of *Bacteroides dorei* can be similarly recited as the probe, that can specifically detect *Bacteroides vulgatus* and *Bacteroides dorei*.

The primers or probes constituting the test drug of the present invention may contain an additional sequence (nucleotide sequence that is not complementary to the polynucleotide to be detected) within the range, that does not prevent specific detection.

The polynucleotide, that is used as the aforementioned primers or probes, may be deoxyribonucleic acid (DNA) or ribonucleic acid (RNA). In the case of ribonucleic acid, the thymidine residue (T) in the nucleotide sequence is appropriately replaced with the uridine residue (U). It may also be a DNA containing a uridine residue synthesized by changing T at any position to U. Similarly, it may be RNA containing a thymidine residue synthesized by changing U at any position to T. In addition, point mutation such as deletion, insertion, or substitution, and modified nucleotide may be present in the polynucleotide as long as the specificity of hybridization does not decrease.

The primers or probes may be labeled with a suitable label, for example, radioisotope (e.g., $^{125}$I, $^{131}$I, $^{3}$H, $^{14}$C, $^{32}$P, $^{33}$P, $^{35}$S, etc.), enzyme (e.g., β-galactosidase, (β-glucosidase, alkaline phosphatase, peroxidase, malate dehydrogenase, etc.), fluorescent substance (e.g., fluorescamine, fluorescein isothiocyanate etc.), luminescent substance (e.g., :luminol, luminol derivative, luciferin, lucigenin etc.), biotin, and the like.

The nucleic acid to be used as the aforementioned primers or probes can be chemically synthesized using, for example, a general-purpose DNA synthesizer. The nucleic acid may be synthesized using any other well known method in the pertinent technical field.

The test drug of the present invention may further contain a nucleic acid synthase (DNA polymerase, RNA polymerase, reverse transcriptase, and the like), other enzymes, a substrate (dNTP, rNTP, etc.) corresponding to the enzyme, and the like as other components. It may also contain a label detection substance, a buffer solution and the like.

In another embodiment, *Bacteroides vulgatus* and/or *Bacteroides dorei* can also be detected by an immunological technique known per se and using the antibody, that specifically recognizes the bacterium (hereinafter to be also referred to as "the antibody of the present invention"). The antibody, that specifically recognizes *Bacteroides vulgatus* and/or *Bacteroides dorei*, means the antibody that recognizes and binds to a surface antigen being specifically present on the cell surface layer of the bacterium. Examples of such surface antigen include polysaccharides being present in the cell wall, peptidoglycan, proteins, and the like. Alternatively, it is not limited to a surface antigen, and may be the antibody, that recognizes and binds to a component specific to *Bacteroides vulgatus* and/or *Bacteroides dorei*. Such specific antibody can be obtained by preparing the polyclonal antibody or the monoclonal antibody by a production method known per se and using *Bacteroides vulgatus* or *Bacteroides dorei* or a processed bacterial product thereof as an immunogen, and selecting from the obtained antibody clones, a clone that does not cross-react with related species other than *Bacteroides vulgatus* and/or *Bacteroides dorei*. The antibody of the present invention includes natural antibodies, as well as antibody fragments with specific binding activity, specifically, F(ab')$_2$, Fab', Fab, Fv, sFv, dsFv, sdAb, and the like. The class of antibody is not particularly limited, and includes antibodies having any isotype such as IgG, IgM, IgA, IgD, and IgE. IgG or IgM is preferable, and IgG is more preferable in view of the ease of purification and the like.

Using the antibody of the present invention, detection, quantification, and the like of *Bacteroides vulgatus* and/or *Bacteroides dorei* can be performed by an immunological method. Examples of the immunological method include, but are not limited to, flow cytometry analysis, radioisotope immunoassay method (RIA method), ELISA method (Methods in Enzymol. 70: 419-439 (1980)), Western blotting, immunohistostaining, and the like.

When the presence of bacterium in which the abundance of *Bacteroides vulgatus* and *Bacteroides dorei* in the intestinal microflora of the test subject is lower than the normal values (e.g., cutoff value (e.g., mean-2SD etc.) determined by the amount of the bacterium in the intestinal microflora of a healthy human population) was confirmed by any of the above-mentioned methods, the test subject can be judged to have developed an LPS-associated disease or has a high risk of developing the disease in the future. Conversely, when these two species show more than the cutoff value, the test subject can be judged to have not developed LPS and the risk of developing LPS in the future is less.

Examples of the LPS-associated disease include circulatory diseases, such as atrial fibrillation, cardiac failure, ischemic cardiac diseases, myocardial infarction, angina pectoris, hypertension, arteriosclerosis, aneurysm of aorta, aortic dissection, arteriosclerosis obliterans, aortic stenosis, and the like, inflammatory diseases, such as, for example, hepatitis, non-alcoholic steatohepatitis, fatty liver, liver cancer due to progression of hepatitis, intestinal inflammation, irritable bowel syndrome, gastritis, collagen disease, chronic rheumatoid arthritis, chronic nephritis, IgA nephropathy, bronchial asthma, interstitial pneumonia, drug-induced lung disorder, pulmonary infiltration with eosinophilia syndrome, atypical mycobacteriosis, allergic rhinitis, atopic dermatitis, sepsis, and the like, metabolic diseases, such as diabetes, obesity, metabolic syndrome, lifestyle-related disease, dyslipidemia, osteoporosis, and the like, and the like.

The present invention is explained in more detail by referring to following Examples. The Examples are mere exemplifications of the present invention and do not limit the scope of the present invention in any manner.

EXAMPLES

Material and Method
Recruitment of CAD Patients and the Controls

All participants provided a written informed consent after the registration. The study was conducted according to the guidelines of the Declaration of Helsinki. This study was approved by the Ethics Committee of Kobe University (approval number 1595) and registered with the University hospital Medical Information Network Clinical Trials Registry (test registration No. 000015703, URL: http://www.umin.ac.jp/ctr/).

Thirty CAD patients and 30 non-CAD controls with coronary risk factors were recruited at Kobe University Hospital from October 2014 to July 2015. The CAD group included stable angina pectoris patients and the patients with old myocardial infarction with conserved left ventricular ejection fraction (>40%), who underwent percutaneous coronary intervention or coronary artery bypass graft surgery at least 6 months before this study. Patients with acute coronary syndrome were excluded. Single-vessel or multi-vessel disease was defined in terms of the number of major coronary arteries showing stenosis exceeding 75% on diagnostic coronary angiography.

Thirty patients with coronary risk factors such as hypertension, diabetes and/or dyslipidemia but no current or previous history of coronary artery disease or other vascular disease were recruited as age- and gender-matched controls. The history of coronary artery disease or other vascular diseases was defined as a confirmed vascular disease, a symptom indicating angina pectoris, an electrocardiographic abnormality indicating old myocardial infarction or angina pectoris, or abnormality on chest X-ray.

Patients with systemic diseases including hepatic diseases, renal diseases (serum creatinine levels>2.0 mg/dL), collagen disease, or cancer were excluded from the study. Patients treated with antibiotics were also excluded. Diabetes mellitus was defined by the glycohemoglobin value>6.5%, use of an oral antidiabetic drug, or insulin treatment, according to National Glycohemoglobin Standardization Program Index. The blood pressure>140/90 mmHg or the use of a depressor was defined as hypertension. According to the guideline published by Japan Atherosclerosis Society, low density lipoprotein cholesterol levels>140 mg/dL, triglyceride levels>150 mg/dL or use of an antidyslipidemic drug was defined as dyslipidemia.

DNA Extraction from Fecal Samples

The test subject was hospitalized, and the fecal samples derived from the test subject were collected while the subject ingested hospital food. The fecal samples derived from mice were collected at 6 and 16 weeks of age. These fecal samples were stored at −80° C. DNA extraction from the fecal samples was performed by the Nihon Gene Research Laboratories Inc according to the previously established procedures (Appleid and Environmental Microbiology 63, 2802-2813 (1997); Appl Environ Microbiol 71, 4153-4155 (2005); FEMS Microbiology Ecology 68, 351-362 (2009)). For each sample, the cellular DNA was extracted from 0.2-0.3 g of fecal materials by using G'NOMEs kit (BIO 101, La Jolla, Calif.) and according to the manufacturer's instructions after minor modification. Briefly, the fecal samples were homogenized in the provided cell suspension, cell lysing/denaturing solution was added, and the samples were incubated at 55° C. for 30 min. To improve cell lysis, 750 mL of silica beads (0.1 mm diameter) were added and the mixture was shaken for 10 min at the maximum speed in a BeadBeater apparatus (BioSpec, Bartlesville, Okla.). Polyvinylpyrrolidone (15 mg) was added to ensure removal of the polyphenol contamination, which was able to inhibit subsequent quantitative PCR. The samples were vortexed and centrifuged at 20,000 g for 3 min and the supernatant was collected. The residual pellets were washed with 400 mL of TENP buffer (50 mM Tris buffer, pH 8, 20 mM EDTA, pH 8, 100 mM NaCl, 1% polyvinylpolypyrrolidone) and centrifuged at 20,000 g for 3 min. The washing step was repeated once more and the obtained supernatants were pooled. The nucleic acid was precipitated by adding an equal volume of isopropanol, stored at −20° C. for 10 min, and then centrifuged at 20,000 g for 5 min. The pellets were resuspended in a mixture of 400 mL of distilled water and 100 mL of salting out agents and incubated at 4° C. for 10 min. The sample was centrifuged at 20,000 g for 10 min and the supernatant containing the DNA was transferred to a clean 1.5 mL centrifuge tube. Two-fold volume of 100% ethanol was added, and the mixture was allowed to stand at room temperature for 5 min to precipitate DNA, and then centrifuged at 20,000 g for 5 min. The DNA was redissolved in 150 mL of TE buffer and the DNA solution was stored at −20° C. until later analysis.

16S rRNA Gene Amplification and Pyrosequencing

A portion of the 16S rRNA gene (V3-V4 region, corresponding to positions 342 to 806 of the *Escherichia coli* numbering system) was amplified by PCR using the non-denaturing universal primer set of 342F and 806R (Table 2) (see, DNA Res. 21, 217-227 (2014) for the details of primer set and PCR conditions). After adding the sequencing adapter, the amplicons were sequenced by Takara Bio Inc. using Illumina MiSeq platform (Illumina Inc., San Diego, Calif.) according to the manufacturer's protocol.

Using USEARCH version 10.0.240 (Bioinformatics. 26, 2460-2461 (2010)) version 0.33 (parameter: LEADING:17 TRAILING:17 AVGQUAL:25 MINLEN:100), the bacterial composition matrix was produced. Also, high quality 16S rRNA gene amplicon sequence generated using Trimmomatic (Bioinformatics. 30, 2114-2120 (2014)) was selected using the previous protocol. For the remaining reads, fastq_mergepairs command of USEARCH (parameter: default value) was used. Then, Tagcleaner (BMC Bioinformatics. 11, 341 (2010)) version 0.16 (parameter: tag5 CTACGGGGGGCAGCAG (SEQ ID NO: 51) mm5 3-tag3 AGATACCCCGGTAGTCC (SEQ ID NO: 52) mm3 3-nomatch 3) was used to remove sequences having no primer region. Thereafter, an internal python script was used to remove the sequence having N. Using the filter_phix command of USEARCH, Phixread was removed. Using the command sort by length of USEARCH (parameter: minseqlength 300), short sequences were removed. Finally, the UTUSE algorithm (fastx_unique command and otu_cluster command (parameter: -minsize 1)) was used to generate an OTU table (Nat Meth. 10, 996-998 (2013)). The each representative sequence of the OTUs was annotated to the genus of bacteria with a bootstrap value of ?0.5 using RDP Classifier version 2.12 (Appl Environ Microbiol. 73, 5261-5267 (2007)). In addition, using BLASTN version 2.2.25, each representative sequence of each OUT was annotated to reference database silva Living Tree Project version 123 (Syst Appl Microbiol. 31, 241-250 (2008)) with identity threshold ?97% and coverage ?80%.

Analysis of Short Chain Fatty Acid in Fecal Samples

Fecal samples were collected after the test subjects began to eat hospital-assigned diet in the hospital. The samples were diluted with sterilized water containing 2-ethylbutyric acid as an internal control, and then labeled with 2-nitrophenylhydrazine using YMC-Pack FA kit (#0 XSRFAR01, YMC, Kyoto, Japan). The short chain fatty acid in the sample was quantified by liquid chromatography (Prominence LC-20AD; Shimadzu, Kyoto, Japan).

Animals

All the apolipoprotein E-deficient (Apoe$^{-/-}$) mice used had C57BL/6 background. All the mice were housed in an SPF grade animal facility within Kobe University Institute. The animals were fed with a normal diet (CLEA Japan, Inc.) and allowed free access to water under a strict 12-hr light cycle. 6-week-old mice were divided into three treatment groups, the control group, where mice orally ingested a medium, the genus *Bacteroides* live bacterium group, where mice orally ingested live *Bacteroides vulgatus* and *Bacteroides dorei*, and the *Bacteroides* heat-killed bacteria group, where mice orally ingested heat-sterilized *Bacteroides vulgatus* and *Bacteroides dorei*, each at a dose of $2.5 \times 10^9$ cfu/100 μl times a week. All experiments were conducted according to the guideline (guideline No. P160701) for effective animal experiments in Kobe University School of Medicine.

The obese mouse model and the non-alcoholic steatohepatitis (NASH) mouse model were prepared using C57BL/6J mice (Japan Charles River company) by the method described in detail later.

Culture and Preparation of *Bacteroides vulgatus* and *Bacteroides dorei*

*Bacteroides vulgatus* (#8482; American Type Culture Collection, Manassas, Va., and NTZ002 strain (deposit number: NITE BP-02863)) and *Bacteroides dorei* (#17855; Deutsche Sammlung von Mikroorganismen, Braunschweig, Germany, and NTZ001 strain (deposit number: NITE BP-02862)) were anaerobically cultured in Difco™ reinforced clostridial medium (#218081; BD Bioscience, San Jose, Calif.) at 37° C. An anaerobic chamber (Coy Laboratory Products, Grass Lake, Mich.) containing 10% $CO_2$, 10% hydrogen and 80% nitrogen was used for all anaerobic microbial processes. *Bacteroides vulgatus* and *Bacteroides dorei* were heat-sterilized by treating at 121° C. for 15 min. Successful heat sterilization was confirmed by a failure to grow after plating the heat-treated bacteria.

Evaluation of Biochemical Parameters and Cytokine Levels in Plasma

Animals were fasted overnight and blood was collected in a heparin tube by cardiac puncture under anesthesia. The blood samples were centrifuged at 3,000 rpm, 4° C. for 10 min, and stored at -80° C. until measurement. The plasma concentration of total cholesterol, high density lipoprotein cholesterol, low density lipoprotein cholesterol, and triglyceride were enzymatically measured using an automated chemical analyzer (SRL). Plasma cytokine levels were analyzed using cytometric bead array kit (BD Bioscience) and according to the manufacturer's instructions.

Evaluation of Arteriosclerosis Lesions

The mice were anesthetized, the aortas were perfused with physiological saline, and the region from the center of the left ventricle to the branch point of the iliac artery was excised. To analyze lesions of the aortic root, a sample from the proximal ascending aorta to the aortic sinus was obtained. The sample was embedded in an embedding medium for the preparation of a frozen tissue section, OCT compound (#4583, Tissue-Tek; Sakura Finetek, Tokyo). Five pieces of consecutive sections (thickness 10 μm) of the aortic sinus over 550 μm were collected from each mouse and stained with oil red O (#154-02072; Sigma-Aldrich, St. Louis, Mo.) or hematoxylin (#3000; Muto Chemical, Tokyo). The stained sections were digitally captured using an all-in-one fluorescence microscope (#BZ-8000; Keyence, Osaka). To quantitatively analyze the degree of arteriosclerosis, ImageJ (registered trademark) software was used as previously reported (Circulation. 120, 1996-2005 (2009)). Total lesion area in five separate sections obtained from each mouse was calculated. For en face lesion analysis, an aortic segment extending from the proximal ascending aorta to the common iliac artery bifurcation was excised and fixed in 10% formalin buffer. The adventitial tissue was carefully removed, the aorta was longitudinally dissected, stained with oil red O, pinned on a black wax surface, and captured using a digital camera. The stained lesion area was shown as a percentage of the total area, and the measurement was performed using ImageJ (registered trade mark) software as previously reported (Circulation. 120, 1996-2005 (2009)).

Immunohistochemical Analysis of Arteriosclerotic Lesions

Immunohistochemical analysis of arteriosclerotic lesions was performed using macrophage detection antibody (MOMA-2, #T-2029, 1:400; BMA Biomedicals, Augst, Switzerland) and T cell detection antibody (CD4, #550278, 1:100; BD Biosciences) on acetone-fixed or formalin-fixed 10 μm frozen sections of mouse aortic roots. The detection was performed using biotinylated secondary antibody (#ab102250, 1:500; abcam, Cambridge, UK) and streptavidin-labeled horseradish peroxidase (#P0397, 1:500; Dako Co., Carpinteria, Calif.). The stained sections were digitally captured using an all-in-one fluorescence microscope. In MOMA-2 staining, the percentage of stained area to the total arteriosclerotic lesion area was calculated. The quantification of CD4-positive T cells was performed by counting the number of stained cells in each section.

Histological Analysis of Mouse Colon

In each mouse, the ascending colon was excised at 16 weeks of age and embedded in OCT compound. Immunofluorescence staining was performed on an acetone-fixed 10 μm frozen section by using an antibody for detection of the tight junction protein (anti-ZO-1, #sc-33725, 1:100; Santa Cruz Biotechnology, Santa Cruz, Calif.). The detection was performed using a secondary antibody conjugated to Cy3 (#405408, 1:200; BioLegend, San Diego, Calif.). Using DAPI (#H-1200; Vector Laboratories Inc., Burlingame, Calif.), nuclear staining was performed. The stained section was digitally captured using an all-in-one fluorescence microscope. The expression intensity of ZO-1 was analyzed using ImageJ (registered trade mark) software.

Flow Cytometry

Mesenteric lymph node (MLN) cells, splenocytes, and RAW264.7 cells were incubated with an anti-CD16/CD32 antibody (clone 2.4G2; #553142; BD Biosciences) to block Fc receptors. For the detection of surface antigens, $10 \times 10^5$ MLN cells or splenocytes in 50 µL of phosphate buffered saline (PBS) containing 2% fetal bovine serum (FBS) were stained with the following antibodies (BD Biosciences or eBioscience):

anti-CD4 (clone RM4-5; Cat 557871)
    anti-CD11b (clone M1/70; #557396)
    anti-CD11c (clone HL3; #558079)
    anti-CD44 (clone IM7; #553134)
    anti-CD62L (clone MEL-14; #553150)
    anti-CD69 (clone FN50; #555533)
    anti-CD80 (clone 16-10A1; #560016)
    anti-CD86 (clone GL1; #553692)
    anti-CD273 (clone TY25; #560086)
    anti-CD274 (clone MIH5; #558091)
    anti-F4/80 (clone BM8; #17-4801-82)
    anti-Ly6G (clone RB6-8C5; #12-5931-82)
    anti-TLR4 (clone MTS510, #17-9924-82).

Using Foxp3/Transcription Factor Staining Buffer Set (#00-5523-00, eBioscience, San Diego, Calif.) or Fixation/Permeabilization Solution Kit (#554714, BD Biosciences), anti-Foxp3 antibody (clone FJK-16; #17-5773-82; eBioscience), and anti-CTLA-4 antibody (clone UC10; BD Biosciences; #553720), intracellular staining was performed according to the manufacturer's instructions. An isotype-matched antibody was used as a control. Proliferation of RAW264.7 cells was tested using anti-Ki67 set (clone B56; #556027) and according to the manufacturer's instructions. Flow cytometry analysis was performed using Attune (registered trade mark) acoustic focusing cytometer (Life Technologies, Grand Island, N.Y.) and FlowJo software (Tree Star, Inc., Ashland, Oreg.).

In Vivo Intestinal Permeability Assay

After fasting overnight, fluorescein isothiocyanate (FITC)-labeled dextran (FD4, 500 mg/kg of body weight; Sigma-Aldrich) was orally given to the mice. After 4 hr, the concentration of FD4 in the plasma was measured using a fluorescence spectrophotometer (EnSpire; PerkinElmer, Inc., Waltham, Mass.) at excitation wavelength 490 nm and fluorescence wavelength 520 nm.

Preparation of Fecal Supernatant

The same human fecal sample was used for LPS measurement and 16S rRNA gene sequencing. Mouse fecal samples were collected 24 hr after the last oral ingestion from 16-week-old control mice and *Bacteroides*-treated mice, or 6-week-old antibiotic (AVNM)-treated mice. A fecal supernatant was obtained by slightly modifying the previously reported protocols (PLoS One. 7, e47713 (2012); Gut. 63, 1069-1080 (2014); BMC Microbiol. 16, 9 (2016)). Briefly, fecal samples were suspended in sterile PBS to a concentration of 50 mg/500 µL and gently vortexed to prevent disruption of bacterial cells. After centrifugation at 3,000 rpm for 15 min, the supernatant was collected, sterilized by filtration through a 0.45 µm filter and then a 0.22 µm filter, inactivated by incubation at 70° C. for 15 min, and stored at −80° C. In addition, a mouse cecal feces sample was collected from 16-week-old control mice and *Bacteroides*-treated mice by a conventional method.

Analysis of LPS Levels in Plasma and Fecal Supernatant

LPS levels in plasma and feces were measured using the Limulus Amebocyte Lysate Assay Kit (#K50-643J; Lonza Inc., Basel, Switzerland) and according to the manufacturer's instructions. Plasma was diluted 10-fold and fecal supernatant was diluted 10,000-fold in pyrogen-free water and inactivated at 70° C. for 15 min. LPS measurement was performed in pyrogen-free glass tubes, Eppendorf tubes and plates.

In Vitro Fecal Supernatant Stimulation and siRNA Assay

RAW264.7 macrophage was cultured in RPMI-1640 medium containing 10% FBS. For proliferation, RAW264.7 cells ($1 \times 10^5$ cells) were seeded in 24-well flat bottom plate (Corning Costar, Corning, N.Y.), and incubated in the presence of a fecal supernatant at 37° C. in 5% $CO_2$ atmosphere for 5 hr. For cytokine production analysis, TLR4 knockdown was performed with RNAiMAX reagent (#13778030, Invitrogen) and using siRNA against TLR4 (#4390771; Invitrogen, Carlsbad, Calif.). Silencer™ Select Negative Control No. 1 siRNA (#4390843, Invitrogen) was used as a control. HT29 human intestinal epithelial cells were purchased from American Type Culture Collection (ATCC), and cultured in 10% FBS-containing RPMI-1640 medium. The HT29 cells were seeded in a 24-well flat bottom plate, and incubated in the presence of fecal supernatant in 37° C., 5% $CO_2$ atmosphere for 24 hr.

RNA Extraction and Real-Time PCR Analysis

Using TRIzol™ reagent (#15596018; Thermo Scientific, Waltham, Mass.), total RNA was extracted from tissue or cell samples according to the manufacturer's instructions. Using PrimeScript reverse transcription reagent kit (#RR037A; Takara, Shiga), cDNA was synthesized. Using SYBER Premix Ex Taq (#RR820; Takara) and LightCycler (registered trade mark) 96 System (#05815916001; Roche, Mannheim, Germany), quantitative RT-PCR was performed according to the manufacturer's instructions. Specific primers for each gene are shown in Table 2. The expression data was normalized with GAPDH, which is a control housekeeping gene, and analyzed by the ΔΔT method.

TABLE 2

| gene | Primer sequences (5' - 3') | |
|---|---|---|
| CCL2 (mice) | forward: GCA TCC ACG TGT TGG CTC A | [5][a] |
| | reverse: CTC CAG CCT ACT CAT TGG GAT CA | [6] |
| CCL17 (mice) | forward: CCG AGA GTG CTG CCT GGA TTA | [7] |
| | reverse: AGC TTG CCC TGG ACA GTC AGA | [8] |
| CCL21 (mice) | forward: CCA ACT TGC AGC TGT CCA TCT C | [9] |
| | reverse: CAT CAC TGC CTT GGG TCC AG | [10] |
| CCR7 (mice) | forward: GGT GGT GGC TCT CCT TGT CAT T | [11] |
| | reverse: ACA CCG ACT CGT ACA GGG TGT AGT C | [12] |
| CD11c (mice) | forward: AGA CGT GCC AGT CAG CAT CAA C | [13] |
| | reverse: CTA TTC CGA TAG CAT TGG GTG AGT G | [14] |

TABLE 2-continued

| gene | Primer sequences (5' - 3') | |
|---|---|---|
| CD80 (mice) | forward: AGT TTC CAT GTC CAA GGC TCA TTC | [15] |
| | reverse: TTG TAA CGG CAA GGC AGC AAT A | [16] |
| CD86 (mice) | forward: TGG CAT ATG ACC GTT GTG TGT G | [17] |
| | reverse: ACG TTT GAG CAG ATG GAA ACT CTT G | [18] |
| Claudin 1 (mice) | forward: TCT ACG AGG GAC TGT GGA TG | [19] |
| | reverse: TCA GAT TCA GCA AGG AGT CG | [20] |
| F4/80 (mice) | forward: CTT TGG CTA TGG GCT TCC AGT C | [21] |
| | reverse: GCA AGG AGG ACA GAG TTT ATC GTG | [22] |
| Foxp3 (mice) | forward: CTC ATG ATA GTG CCT GTG TCC TCA A | [23] |
| | reverse: AGG GCC AGC ATA GGT GCA AG | [24] |
| GAPDH (mice) | forward: TGT GTC CGT CGT GGA TCT GA | [25] |
| | reverse: TTG CTG TTG AAG TCG CAG GAG | [26] |
| GAPDH (human) | forward: TGA ACG GGA AGC TCA CTG G | [27] |
| | reverse: TCC ACC ACC CTG TTG CTG TA | [28] |
| ICAM (mice) | forward: CAA TTC ACA CTG AAT GCC AGC TC | [29] |
| | reverse: CAA GCA GTC CGT CTC GTC CA | [30] |
| IL-1b (mice) | forward: TCC AGG ATG AGG ACA TGA GCA C | [31] |
| | reverse: GAA CGT CAC ACA CCA GCA GGT TA | [32] |
| IL-6 (mice) | forward: CCA CTT CAC AAG TCG GAG GCT TA | [33] |
| | reverse: GCA AGT GCA TCA TCG TTG TTC ATA C | [34] |
| IL-17 (mice) | forward: ACG CGC AAA CAT GAG TCC AG | [35] |
| | reverse: CTC AGC AGC AGC AAC AGC ATC | [36] |
| Occludin (mice) | forward: ATG TCC GGC CGA TGC TCT C | [37] |
| | reverse: TTT GGC TGC TCT TGG GTC TGT AT | [38] |
| TLR4 (mice) | forward: GGG CCT AAA CCC AGT CTG TTT G | [39] |
| | reverse: GCC CGG TAA GGT CCA TGC TA | [40] |
| TNF-α (mice) | forward: AAA CTG GTC GGG CAA TTC TG | [41] |
| | reverse: AGG GTT GGA CAC CTG AAT GCT A | [42] |
| Universal 16S rDNA | forward: CTA CGG GGG GCA GCA G | [43] |
| | reverse: GGA CTA CCG GGG TAT CT | [44] |
| VCAM1 (mice) | forward: TGC CGG CAT ATA CGA GTG TGA | [45] |
| | reverse: CCC GAT GGC AGG TAT TAC CAA G | [46] |
| ZO-1 (mice) | forward: TTT TTG ACA GGG GGA GTG G | [47] |
| | reverse: TGC TGC AGA GGT CAA AGT TCA AG | [48] |
| ZO-1 (human) | forward: GAA TGA TGG TTG GTA TGG TGC G | [49] |
| | reverse: TCA GAA GTG TGT CTA CTG TCC G | [50] |

[a]The number in [ ] indicates SEQ ID NO.

Western Blotting

Western blot analysis was performed as described in detail in Sci. Rep. 7, 12989 (2017). Briefly, cells were rinsed twice with PBS and collected in ice-cooled lysis buffer (20 mM HEPES, pH 7.4; 1% NP40; 1% SDS; and 150 mM NaCl). Proteins extracted from total lysates were subjected to 6% SDS-PAGE and transferred onto polyvinylidene difluoride membrane (#IB401002; Thermo Scientific) by using iBlot (registered trade mark) Gel Transfer Device (Thermo Scientific). The membrane was blocked with 5% milk (#31149-75; Nacalai Tesque, Kyoto), incubated with the primary antibodies at 4° C. overnight, and incubated with the horseradish peroxidase-conjugated secondary antibody at room temperature for 1 hr. After incubation with Immobilon Western HRP Substrate (#WBKLS0500; Merck Millipore, Billerica, Mass.), the signal was detected using V3 Western Workflow system (Bio-Rad, Hercules, Calif.). In this experiment, the following primary antibodies were used.

anti-ZO-1 (#8193, 1:1,000; Cell Signaling Technology, Danvers, Mass.)

anti-β-actin (#A5441, 1:5,000; Sigma-Aldrich)

The band intensity was quantified using ImageJ (registered trade mark) software.

Statistical Analysis

Statistical analysis was performed using R software, version 3.1.0 (http://www.r-project.org/), JMP version 10 (SAS Institute, Cary, N.C.), and Prism version 7.0 (GraphPad Software; San Diego, Calif.). Whether the data shows normal distribution was determined using Shapiro-Wilk test. The results of the normal distribution data are shown by the mean±standard error of the mean or mean±standard deviation of normal distribution data, and the nonnormal distribution data are shown by median±the interquartile range (range from first to third quartile). 2-tailed Student's t-test was used for normal distribution data and Mann-Whitney U-test was used for non-normal distribution data to evaluate significant difference between the two groups. Categorical variables were compared using Fisher's exact test or $\chi^2$ test. Values of P<0.05 were considered statistically significant for all tests. To evaluate the statistical correlation between two parameters, single regression/single correlation was calculated using the least-squares method, and the results are shown in Pearson's correlation coefficient. One-way analysis of variance (ANOVA) was used to detect significant differences among the three groups. The q value was calculated using Benjamini-Hochberg method, and p value for multiple comparison was adjusted. Clustering of data from 30 CAD patients and 30 controls was performed at the genus level as described in Arthritis Rheumatol. 68, 2646-2661 (2016).

Results

Intestinal Microflora Profile in CAD Patients

30 CAD patients, and 30 non-CAD patients with coronary risk factors such as hypertension, diabetes, or dyslipidemia and having the same age and gender were recruited as the test subjects. 16S rRNA gene sequencing in fecal samples was used to compare the intestinal bacterial profiles of these test subjects in detail. The background of the subjects is shown in Table 3.

TABLE 3

| Variables | Non-CAD Ctrls (n = 30) | CAD (n = 30) |
| --- | --- | --- |
| Age (years) | 62.9 ± 6.8 | 63.6 ± 7.2 |
| Sex, male (%) | 77 | 90 |
| BMI (kg/m$^2$) | 24.8 ± 4.1 | 25.1 ± 2.8 |
| AST (U/l) | 22.9 ± 5.6 | 27.8 ± 13.7 |
| ALT (U/l) | 23.2 ± 11.6 | 27.3 ± 17.1 |
| BUN (mg/dL) | 16.2 ± 4.4 | 14.9 ± 3.7 |
| Creatinine (mg/dL) | 0.94 ± 0.26 | 0.87 ± 0.16 |
| HDL-C (mg/dL) | 52.4 ± 13.8 | 50.8 ± 19.2 |
| LDL-C (mg/dL) | 113.8 ± 35.7 | 91.9 ± 26.1** |
| TG (mg/dL) | 145.6 ±73.6 | 150.3 ± 75.7 |
| HbA1c (NGSP %) | 6.55 ± 1.30 | 6.35 ± 0.86 |
| CRP (mg/dL) | 0.15 ± 0.20 | 0.09 ± 0.09 |
| History of smoking (%) | 70 | 77 |
| Current smoker (%) | 13 | 13 |
| Past history | | |
| Diabetes Mellitus (%) | 40 | 37 |
| Dyslipidemia (%) | 60 | 93** |
| Hypertension (%) | 77 | 87 |
| Medications | | |
| ACE-I/ARB (%) | 57 | 53 |
| Anti-diabetic medications (%) | 37 | 30 |
| Anticoagulant or Antiplatelet (%) | 57 | 100*** |
| β-blocker (%) | 30 | 53 |
| Calcium channel blocker (%) | 47 | 63 |
| PPI/H2 blocker (%) | 43 | 97*** |
| Statin (%) | 40 | 90*** |

*p < 0.05;
**p < 0.01;
***p < 0.001

To analyze the intestinal bacterial profile of the test subjects, the samples were classified into three clusters at the genus level according to the procedure reported previously (Nature. 473, 174-180 (2011)) (FIG. 1a). Each cluster was characterized by the abundance of the following specific genera (FIG. 1b).

cluster 1: genus *Bacteroides*
cluster 2: genus *Prevotella*
cluster 3: genus *Faecalibacterium*, genus *Ruminococcus*, or genus *Bifidobacterium*

Non-CAD controls were more categorized in cluster 1, whereas CAD patients were rarely categorized in this cluster (FIG. 1c). The a diversity, Bacteroidetes/Firmicutes ratio, Gram-positive bacteria/Gram negative bacteria ratio, and the short chain fatty acid concentration in feces were not significantly different between the two groups. A comprehensive comparison of the abundances at the genus and species levels between the CAD group and non-CAD group revealed that the relative abundance of the genus *Bacteroides* tended to be low in CAD patients compared to the controls (FIG. 1d). As a result of principal component analysis, the abundance of major species in the intestinal microbiome was different between the two groups, and it was clarified that *Bacteroides vulgatus* and *Bacteroides dorei* relatively decreased and *Fecalibacterium plausnitzii* and *Prevotella copri* were enriched in CAD patients (FIG. 6). In consideration of the previous reports indicating the low abundance of the genus *Bacteroides* in arteriosclerosis patients, the present inventors focused on the *Bacteroides* species, *Bacteroides vulgatus* and *Bacteroides dorei*. These species are involved in the anti-inflammatory response (Cell. 165, 842-853 (2016)) and are the most abundant species in the genus *Bacteroides* (FIG. 1e), and their abundance was significantly low in CAD patients (FIG. 1f). Since these two species have a similar 16S rRNA sequencing pattern (Int J Syst Evol Microbiol. 56, 1639-1643 (2006)), the methodology used by the present inventors wasn't able to distinguish the two. Thus, the present inventors constructed a mouse model by oral ingestion of *Bacteroides vulgatus* and *Bacteroides dorei* to mice showing a tendency toward arteriosclerosis and, using the mouse model, tried to confirm the causal relationship between these species and arteriosclerosis and to elucidate the underlying mechanism.

Oral Ingestion of Live Bacteria of *Bacteroides vulgatus* and *Bacteroides dorei* Suppresses the Formation of Arteriosclerotic Plaque To judge the effects of *Bacteroides vulgatus* and *Bacteroides dorei* on the onset of arteriosclerosis, 6-week-old female apolipoprotein E-deficient (Apoe−/−)) mice were made to orally ingest live or heat-killed bacteria of *Bacteroides vulgatus* ATCC 8482$^T$ strain and *Bacteroides dorei* DSM 17855$^T$ strain 5 times per week for 10 weeks. According to the same protocol, vehicle (medium) alone was given to the control mice. The mice were euthanized when they were 16 week old, some analyses were performed, and arteriosclerosis and intestinal microflora were evaluated. Compared to the control mice, the mice that orally ingested the live bacteria of genus *Bacteroides* showed no significant difference in the body weight (FIG. 2f) or plasma cholesterol level (FIG. 2g); however, the lesion size significantly decreased in the aortic root and en face analysis of thoracoabdominal aortas (FIG. 2a, b). No significant difference in arteriosclerotic lesion size was observed in the mice that ingested the heat-sterilized genus *Bacteroides*, as compared with the control mice. Furthermore, as a result of immunohistostaining of atherosclerotic lesions in the aortic sinus and subsequent morphological analysis, it was clarified that macrophages and CD4-positive T cells significantly decreased in the mice that orally ingested the genus *Bacteroides*, as compared with the control (FIG. 2c, d). Next, quantitative RT-PCR analysis was performed to evaluate mRNA expression of immunocyte markers and chemokine/chemokine receptors in mouse atherosclerotic aortas. As a result, some atherogenic immunocyte markers and a chemokine/chemokine receptor decreased in the mice that orally ingested the genus *Bacteroides* (FIG. 2e). These results suggest that supplementation of live *Bacteroides vulgatus* and *Bacteroides dorei* by oral ingestion reduces plaque inflammation and thereby suppresses the formation of atherosclerotic lesions.

As a result of 16S rRNA gene sequencing in mouse fecal samples, it was clarified that the composition of the intestinal microflora changed markedly in response to the oral ingestion of *Bacteroides vulgatus* and *Bacteroides dorei* (FIG. 7a, b). Furthermore, the diversity of enteric bacteria decreased in the control mice, whereas that was maintained in the mice fed with live genus *Bacteroides* (FIG. 7c). Surprisingly, the gram-positive bacteria/gram negative bacteria ratio tended to be higher in the mice with oral ingestion of live genus *Bacteroides* than in the control mice (FIG. 7d). The abundance of *Bacteroides vulgatus* and *Bacteroides dorei* was drastically high in the mice with oral ingestion of live genus *Bacteroides* (FIG. 7e).

Live *Bacteroides* Treatment Reduced Colon Lipopolysaccharide (LPS) Levels, Resulting in Reduced Intestinal and Systemic Immune Responses The present inventors previously reported that modulation of the intestinal immune response might prevent arteriosclerosis (Circulation. 120, 1996-2005 (2009); Arterioscler Thromb Vasc Biol. 30, 2495-2503 (2010)). To investigate the mechanism by which *Bacteroides* treatment decreases plaque formation, the present inventors first tested the effect of oral ingestion of *Bacteroides vulgatus* ATCC 8482$^T$ strain and *Bacteroides dorei* DSM 17855$^T$ strain on intestinal immunity. As a result, mRNA expression in the colon of particular antigen-presenting cell markers (CD11c, co-stimulatory molecule CD80) and pro-inflammatory cytokines substantially decreased in the mice, that orally ingested the genus *Bacteroides*, as compared to the control mice (FIG. 3a, b). Furthermore, mRNA expression of CCR7, which is critically important for the transfer of antigen-presenting cells from the intestinal lamina propria to the mesenteric lymph node (MLN), significantly decreased in the mice, that orally ingested the genus *Bacteroides* (FIG. 3a). Thus, the present inventors next tested innate immune responses in MLN. By flow cytometry analysis of MLN, not only the abundance of CD11c high-expressing cells was significantly low, but also the expression of Toll-like receptor 4 (TLR4), MHC class II, and CD80 in the CD11c high-expressing cells decreased significantly in the mice, that orally ingested the live genus *Bacteroides* (FIG. 3c). The expression of cytokine mRNA in MLN also tended to be lower in the mice, that orally ingested the genus *Bacteroides*, than in the control mice (FIG. 3d). These results suggest that live *Bacteroides* treatment suppresses intestinal immune response through inhibition of the antigen-presenting cell activation that is associated with down-regulation of TLR4 expression.

Since LPS stimulates cells through TLR4 and upregulates co-stimulatory molecules on antigen-presenting cells, the present inventors measured fecal LPS levels as an index of colon LPS production by the intestinal microflora. Surprisingly, the fecal LPS level was dramatically lower in the mice, that orally ingested the genus *Bacteroides*, than in the control mice (FIG. 3e). In addition, the present inventors performed in vitro stimulation assay using fecal supernatant, and investigated whether the reduction of colon LPS concentrations after live genus *Bacteroides* treatment was directly reflected in the level of colon inflammation. Stimulation of RAW264.7 macrophage with fecal supernatant significantly inhibited the proliferation of cells treated with fecal supernatant derived from the mice, that orally ingested the genus *Bacteroides* (FIG. 8a). Furthermore, to examine whether LPS/TLR4 signal is a major pathway controlling colon inflammation, siRNA was introduced to produce TLR4 knockdown RAW264.7 macrophages, and the cells were stimulated with fecal supernatant. As a result, by the introduction of non-specific siRNA, secretion of pro-inflammatory cytokines IL-1b, IL-6, and TNF-α remarkably decreased in the macrophage treated with the fecal supernatant, which is derived from the mice treated with live genus *Bacteroides*, rather than RAW264.7 macrophage treated with the fecal supernatant from the control mice. RAW264.7 macrophage introduced with TLR siRNA secreted only a very small amount of pro-inflammatory cytokine, and the amount was significantly low as compared to that of RAW264.7 macrophage introduced with non-specific siRNA (FIG. 8b). These findings suggest that colon LPS concentration controls inflammation of colon through LPS/TLR4 dependent signaling.

Endotoxinemia is known to cause systemic inflammation, disruption of innate and adaptive immunity, and development of arteriosclerosis (Nat Commun. 7, 13436 (2016); Circulation. 133, 2434-2446 (2016); Nat Immunol. 12, 204-212 (2011)). In fact, the plasma LPS level significantly decreased in the mice treated with the genus *Bacteroides* compared to the control mice (FIG. 3f), and the plasma levels of atherogenic cytokines IL-2, IL-4, IL-6, IL-17A, IFN-γ, TNF-α, and the like also decreased (FIG. 3g). Furthermore, the present inventors investigated the source of these cytokines through a flow cytometric assay of splenocytes. As a result, there was no significant difference between the two groups in the proportion of CD11b high expression, F4/80 high expression macrophages, CD11b high expression, Ly6G high expression neutrophils and CD11c high expression dendritic cells (FIG. 9a); however, the mice that orally ingested the genus *Bacteroides* showed decreased expression of MHC class II and co-stimulatory molecule CD86, and increased expression of co-inhibitory molecule programmed death ligand 1 (PD-L1) and PD-L2 on splenic CD11c high-expressing dendritic cells (FIG. 9b). No significant difference was found between the two groups in TLR4 expression on splenic CD11c high-expressing dendritic cells. Consistent with the high tolerogenecity of dendritic cells, the number of CD4-positive T cells also decreased in the mice treated with live genus *Bacteroides* (FIG. 9c). In the mice that orally ingested live genus *Bacteroides*, the number of effector CD44 high expression, CD62L low expression, CD4-positive T cells decreased but the proportion of CD4-positive, CD25-positive, Foxp3-positive regulatory T cells having high levels of intracellular CTLA4 was significantly high (FIG. 9d, e). This indicates that the immune balance is shifting toward suppression. These data suggest that activation of systemic innate immunocytes and suppression of Th1-driven inflammation involved in the onset mechanism of arteriosclerosis are caused by a decrease in the plasma LPS level induced by the treatment with live genus *Bacteroides*.

Live *Bacteroides* Treatment Enhanced Intestinal Barrier In Vitro and In Vivo

Since changes in the composition of the intestinal microflora following intestinal leakiness promote endotoxemia and arteriosclerosis (Circulation. 133, 2434-2446 (2016)), the present inventors next examined whether the live genus *Bacteroides* treatment is effective for intestinal tight junction permeability. As a result, the mice, which orally ingested *Bacteroides vulgatus* ATCC 8482$^T$ strain and *Bacteroides dorei* DSM 17855$^T$ strain, showed a significant decrease in the intestinal permeability of FITC-labeled dextran (FIG. 4a) and a significant increase in the mRNA expression of tight junction gene zo1 (FIG. 4b), as compared to the control mice, which was reflected in the increase in the average fluorescence intensity of ZO-1 in colon (FIG. 4c). These data indicate that the live genus *Bacteroides* treatment strengthens the barrier of tight junction as compared to the state in the control mice. To determine whether changes in the colon LPS concentration affect the formation of tight junction, the present inventors stimulated HT29 human colorectal adenocarcinoma cells having epithelial cell morphology with fecal supernatant. As a result, consistent with the results in vivo, a significantly higher expression level of zo1 (ZO-1) (at mRNA and protein levels) was observed in HT29 cells stimulated with fecal supernatant derived from the mice treated with live genus *Bacteroides* than in HT29 cells stimulated with fecal supernatant derived from the control mice (FIG. 4d, e). These results suggest that changes in colon LPS concentration induced by intestinal microflora possibly affect directly the paracellular permeability through tight junction.

Fecal LPS Levels Increased in CAD Patients

To further investigate the relationship between CAD incidence and LPS production by enteric bacteria in human, the present inventors measured LPS levels in the same fecal samples as those used for 16S rRNA gene sequencing. As a result, the fecal LPS levels in CAD patients were significantly higher than those in the non-CAD control (FIG. 5a). Interestingly, the abundance of the *Bacteroides* species was significantly negatively correlated with fecal LPS levels (R=−0.30, P=0.023). Furthermore, a significant negative correlation was observed between fecal LPS levels and the % abundance of *Bacteroides vulgatus* and *Bacteroides dorei* (R=−0.29, P=0.027) (FIG. 5b). These results strongly suggest that *Bacteroides vulgatus* and *Bacteroides dorei* regulate LPS production by enteric bacteria, and their activity may influence the progression of arteriosclerosis in humans.

Comparative Example

Single Administration of *Bacteroides vulgatus* or *Bacteroides dorei* Did not Significantly Improve Symptoms or Intestinal LPS Levels in Arteriosclerosis Mouse Model By the same method as in the case of the above-mentioned combined administration of the two bacterial species, *Bacteroides vulgatus* ATCC 8482$^T$ strain or *Bacteroides dorei* DSM 17855$^T$ strain was orally ingested individually by Apo$^{-/-}$ mice.

The results are shown in FIG. 10. In any of the single administration groups, the arteriosclerotic lesions in the aortic sinus tended to improve as compared with the control (vehicle administration) group, but no significant difference was found. Furthermore, the fecal (intestinal) LPS level did not decrease by single administration of any species. The expression of tight junction-related genes in the large intestine tended to increase in the *Bacteroides dorei* single administration group as compared with the control group, and the expression of cytokine genes in the large intestine decreased in the *Bacteroides vulgatus* single administration group as compared with the control group. However, a significant difference was not observed in the blood cytokine level of any of the administration groups.

The above results indicate that when *Bacteroides vulgatus* and *Bacteroides dorei* co-exist in the intestine, their effects act synergistically based on different action mechanisms to exert remarkable LPS controllability.

A Variety of Combinations of *Bacteroides vulgatus* and *Bacteroides dorei* all Improved Intestinal LPS Levels in Arteriosclerosis Mouse Model A combination of each bacterium (live bacteria 2.5×10$^9$ CFU/100 µl of each) was orally administered to Apoe−/− ♀ mice or Apoe−/− ♂ mice five times a week. It was administered to Apoe−/− ♀ mice for 10 weeks from 6 weeks to 16 weeks of age, and fecal LPS level was measured at 16 weeks of age. It was administered to Apoe−/− ♂ mice for 7 weeks from 6 weeks to 13 weeks of age, and fecal LPS was measured at 13 weeks of age.

The results are shown in FIG. 12. Not only the type strains (v, d) but also the NT strains (Nv, Nd) showed reduced fecal LPS levels.

Live *Bacteroides* Treatment Improved Intestinal LPS Levels in Arteriosclerotic Mouse Model A combination of *Bacteroides vulgatus* ATCC8482$^T$ and *Bacteroides dorei* DSM 17855$^T$ (live bacteria or dead bacteria, 2.5×10$^9$ CFU/100 µl each as live bacteria) was orally administered to Apoe−/− ♀ mice five times a week. It was administered for 10 weeks from 6 weeks to 16 weeks of age, and fecal LPS and cecal feces LPS were measured at 16 weeks of age. In addition, AVNM (ampicillin, vancomycin, neomycin, and metronidazole) was administered from 5 weeks to 6 weeks of age, and fecal LPS was measured at 6 weeks of age.

The results are shown in FIG. 13. The right and left sides in the Figure respectively show fecal and cecal feces LPS levels of *Bacteroides*-treated Apoe−/− ♀ mice. The center of the Figure shows the fecal LPS level of the Apoe−/− ♀ mice, to which antibiotics were administered. In feces and cecal feces, the amount of LPS decreased when the live bacteria were administered, whereas there was no change from the control (NC) when the dead bacteria were administered.

*Bacteroides* Treatment Improved a Variety of Symptoms of Obesity in Obese Mouse Model Administration to C57BL/6J ♂ mice was performed five times a week for 12 weeks from 6 weeks to 18 weeks of age. A normal diet was administered to the NC group, a high-fat diet HFD (manufactured by Oriental Yeast Co.; containing 60% fat) and a liquid medium used for culturing *Bacteroides vulgatus* or *Bacteroides dorei* at 200 µl/dose were administered to the Ctrl group, a high-fat diet and live bacteria *Bacteroides vulgatus* ATCC8482$^T$ and live bacteria *Bacteroides dorei* DSM 17855$^T$ were orally administered to the B group, and a high-fat diet and live bacteria *Bacteroides vulgatus* NTZ002 strain and live bacteria *Bacteroides dorei* NTZ001 strain were administered to the NB group (FIG. 14-1A).

As a result, the groups to which two strains of the type strain (B) or two strains of the NT strain (NB) were administered in addition to high-fat diet showed suppression of the body weight increase as compared with the Ctrl group (FIG. 14-1B, C).

When a 1 g OGTT test was performed, the groups to which two strains of the type strain (B) or two strains of the NT strain (NB) were administered showed suppression of a sharp rise in the blood glucose level after loading (FIG. 14-1D left), low AUC value (FIG. 14-1D center), and low insulin resistance (HOMA-IR) (FIG. 14-1D right), and improvement of glucose tolerance was confirmed.

When epididymal fat was stained with HE, MACS, or Sirius red (FIG. 14-2E left), the groups to which two strains of the type strain (B) or two strains of the NT strain (NB)

were administered showed a smaller adipocyte size, less number of crown-like structures, and lower fiber formation rate (FIG. 14-2E right).

When the mRNA level of visceral fat (epididymal peripheral fat) was measured, the groups to which two strains of the type strain (B) or two strains of the NT strain (NB) were administered showed low mRNA expression of inflammation cell markers MCP1, F4/80, iNOS, CCR5, and TLR4, as compared with that of the Ctrl group (FIG. 14-2F left), and an increasing tendency of the mRNA expression level of Fizzil (M2 macrophage marker, for which higher level is considered to be anti-inflammatory) (FIG. 14-2F left). Furthermore, the mRNA expression of cytokine IFNγ and TNFα decreased (FIG. 14-2F right).

*Bacteroides* Treatment Improved a Variety of Symptoms of NASH in NASH Mouse Model Administration to C57BL/6J mice was performed five times a week from 8 weeks to 17 weeks of age. A choline-deficient, L-amino acid-defined, high-fat diet (feed for producing NASH model manufactured by EPS EKISHIN Co., Ltd.) was administered as a feed to the Ctrl group, and live bacteria *Bacteroides vulgatus* ATCC 8482$^T$ and live bacteria *Bacteroides dorei* DSM 17855$^T$ were further administered to the *Bacteroides* group.

As a result of anatomy at 17 weeks of age and HE staining of the liver, the Ctrl group showed fatty liver, inflammatory cell infiltration and balloon-like swelling of hepatocytes. However, the group to which two bacteria of the type strain were administered showed marked suppression of inflammatory cell infiltration and balloon-like swelling was not observed (FIG. 15-1 top). The group to which two bacteria of the type strain were administered further showed improvement of NAFLD activity score (NAS) and a significant decrease in the blood AST, AST/ALT ratio, and hepatopathy was markedly suppressed (FIG. 15-1, center, bottom, and FIG. 15-2).

While the present invention has been described with to emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on a patent application No. 2018-022578 filed in Japan on Feb. 9, 2018, the contents of which are incorporated in full herein by reference.

INDUSTRIAL APPLICABILITY

The combination of the present invention is useful as a medicament or functional food for the prophylaxis and/or improvement of circulatory diseases including arteriosclerosis, diseases associated with chronic inflammation, and metabolic diseases associated with abnormalities of metabolism such as glycolipid metabolism. In addition, the test method and the test drug of the present invention are useful since they enable diagnosis and onset risk prediction of the aforementioned diseases through analysis of the microbiome in feces, and provide a non-invasive clinical test method.

The invention claimed is:

1. A method for improving a disease related to an elevated blood or intestinal lipopolysaccharide level in a subject in need thereof, the method comprising oral ingestion by the subject of a live bacterium of *Bacteroides vulgatus* isolated from nature, and a live bacterium of *Bacteroides dorei* isolated from nature.

2. The method according to claim 1, wherein the disease is a circulatory disease, an inflammatory disease, or a metabolic disease.

3. The method according to claim 1, wherein the disease is a circulatory disease selected from the group consisting of atrial fibrillation, cardiac failure, an ischemic cardiac disease, myocardial infarction, angina pectoris, hypertension, arteriosclerosis, aneurysm of aorta, aortic dissection, arteriosclerosis obliterans, and aortic stenosis.

4. The method according to claim 1, wherein the disease is an inflammatory disease selected from the group consisting of hepatitis, non-alcoholic steatohepatitis, fatty liver, liver cancer, intestinal inflammation, irritable bowel syndrome, gastritis, collagen disease, chronic rheumatoid arthritis, chronic nephritis, IgA nephropathy, bronchial asthma, interstitial pneumonia, a drug-induced lung disorder, pulmonary infiltration with eosinophilia syndrome, atypical mycobacteriosis, allergic rhinitis, atopic dermatitis, and sepsis.

5. The method according to claim 1, wherein the disease is a metabolic disease selected from the group consisting of diabetes, obesity, metabolic syndrome, a lifestyle-related disease, dyslipidemia and osteoporosis.

6. The method according to claim 1, wherein the subject is suffering from a circulatory disease, an inflammatory disease, or a metabolic disease, and whose blood and intestinal lipopolysaccharide levels are elevated as compared to those in a control without said disease.

7. The method according to claim 6, wherein the disease is a circulatory disease selected from the group consisting of atrial fibrillation, cardiac failure, an ischemic cardiac disease, myocardial infarction, angina pectoris, hypertension, arteriosclerosis, aneurysm of aorta, aortic dissection, arteriosclerosis obliterans, and aortic stenosis.

8. The method according to claim 6, wherein the disease is an inflammatory disease selected from the group consisting of hepatitis, non-alcoholic steatohepatitis, fatty liver, liver cancer, intestinal inflammation, irritable bowel syndrome, gastritis, collagen disease, chronic rheumatoid arthritis, chronic nephritis, IgA nephropathy, bronchial asthma, interstitial pneumonia, a drug-induced lung disorder, pulmonary infiltration with eosinophilia syndrome, atypical mycobacteriosis, allergic rhinitis, atopic dermatitis, and sepsis.

9. The method according to claim 6, wherein the disease is a metabolic disease selected from the group consisting of diabetes, obesity, metabolic syndrome, a lifestyle-related disease, dyslipidemia and osteoporosis.

\* \* \* \* \*